(12) United States Patent
Kobayashi et al.

(10) Patent No.: US 8,647,867 B2
(45) Date of Patent: Feb. 11, 2014

(54) CELL CULTIVATION METHOD AND CELL CULTURE

(75) Inventors: Naoya Kobayashi, Okayama (JP); Noriaki Tanaka, Okayama (JP)

(73) Assignees: National University Corportion Okayama University, Okayama-shi, Okayama (JP); 3-D Matrix, Ltd., Tokyo (JP)

( * ) Notice: Subject to any disclaimer, the term of this patent is extended or adjusted under 35 U.S.C. 154(b) by 1082 days.

(21) Appl. No.: 11/992,746

(22) PCT Filed: Sep. 29, 2006

(86) PCT No.: PCT/JP2006/319528
§ 371 (c)(1),
(2), (4) Date: Jul. 14, 2008

(87) PCT Pub. No.: WO2007/037407
PCT Pub. Date: Apr. 5, 2007

(65) Prior Publication Data
US 2009/0221068 A1 Sep. 3, 2009

(30) Foreign Application Priority Data

Sep. 30, 2005 (JP) .................. 2005-288156

(51) Int. Cl.
*C12N 5/00* (2006.01)
*C12N 5/02* (2006.01)
*C12N 5/071* (2010.01)

(52) U.S. Cl.
USPC .......................................... 435/325; 435/366

(58) Field of Classification Search
None
See application file for complete search history.

(56) References Cited

U.S. PATENT DOCUMENTS

| 2005/0181973 | A1* | 8/2005 | Genove et al. | 514/2 |
| 2006/0084167 | A1* | 4/2006 | Cohenford et al. | 435/325 |
| 2006/0205071 | A1* | 9/2006 | Hasson et al. | 435/366 |
| 2008/0206733 | A1* | 8/2008 | Tanaka et al. | 435/1.1 |

FOREIGN PATENT DOCUMENTS

| JP | 2003-169847 A | 6/2003 |
| JP | 2005-515796 A | 6/2005 |
| JP | 2005-229871 A | 9/2005 |
| WO | 98/59038 | 12/1998 |
| WO | 02/060396 | 8/2002 |
| WO | WO 02/62969 * | 8/2002 |
| WO | 03/059072 A1 | 7/2003 |
| WO | 2004/007683 A2 | 1/2004 |
| WO | 2005/014615 A2 | 2/2005 |
| WO | 2005/089043 A2 | 9/2005 |
| WO | 2006-082890 A1 | 8/2006 |
| WO | 2007/117565 | 10/2007 |

OTHER PUBLICATIONS

Semino et al. Functional differentiation of hepatocyte-like spheroid structures from putative liver progenitor cells in three-dimensional peptide scaffolds. Differentiation. vol. 71, pp. 262-270, 2003.*
Park, Keun-Hong, "Improved long-term culture of hepatocytes in a hydrogel containing Arg-Gly-Asp (RGD)", *Biotechnology Letters*, vol. 24, pp. 1131-1135, (2002).
Park, Keun-Hong, "Phenotype of hepatocyte spheroids behavior within thermo-sensitive poly(NiPAAm-co-PEG-g-GRGDS) hydrogel as a cell delivery vehicle", *Biotechnology Letters*, vol. 27, pp. 1081-1086, (2005).
Yan, Yongnian, et al., "Direct Construction of a Three-dimensional Structure with Cells and Hydrogel", *Journal of Bioactive and Compatible Polymers*, vol. 20, No. 3, pp. 259-269, (2005).
Bokhari, Maria A., et al., "The enhancement of osteoblast growth and differentiation in vitro on a peptide hydrogel—polyHIPE polymer hybrid material", *Biomaterials*, vol. 26, pp. 5198-5208, (2005).
Qi, Meirigeng, et al., "PVA hydrogel sheet macroencapsulation for the bioartificial pancreas", *Biomaterials*, vol. 25, pp. 5885-5892, (2004).
Kisiday, J., et al., "Self-assembling peptide hydrogel fosters chondrocyte extracellular matrix production and cell division: Implications for cartilage tissue repair", *PNAS*, vol. 99, No. 15, pp. 996-10001, (2002).
Bhandari, et al., Abstract, "Liver tissue engineering: a role for co-culture systems in modifying hepatocyte function and viability," Tissue Eng., (2001), vol. 7, No. 3, Abstract only. 1 page.
"Clonetics aortic endothelial cell systems," Lonza, two (2) pages, http://bio.lonza.com/uploads/tx_mwaxmarketingmaterial/Lonza_BenchGuides_Clonetics_aortic_endothelial_cell_systems.pdf, 2011.
Nussler, et al., Abstract, "The suitability of hepatocyte culture models to study various aspects of drug metabolism," Altex, (2001), vol. 18, No. 2, Abstract only. 1 page.
Riccalton-Banks, et al., Abstract, "Long-term culture of functional liver tissue: three-dimensional coculture of primary hepatocytes and stellate cells," Tissue Eng., (2003), vol. 9, No. 3, Abstract only. 1 page.
Boston Children's Hospital. Adult Stem Cells 101: What are progenitor cells? 2005-2013. http://stemcell.childrenshospital.org/about-stem-cells/adult-somatic-stem-cells-101/what-are-progenitor-cells/ (accessed Jul. 10, 2013), 1 page.
Morshead, Cindi M. "Adult Neural Stem Cells: Attempting to Solve the Identity Crisis." Developmental Neuroscience 26 (2004): 93-100.

(Continued)

*Primary Examiner* — Anne Gussow
*Assistant Examiner* — Channing S Mahatan
(74) *Attorney, Agent, or Firm* — Nath, Goldberg & Meyer; Tanya E. Harkins

(57) ABSTRACT

Provided is a cell cultivation method in which the cell is cultured using a peptide hydrogel as a scaffold, for carrying out high-dimensional culture of a cell such as porcine hepatocyte, human hepatocyte, porcine pancreatic islet or human pancreatic islet for a long period under conditions where cell survival, cell morphology and cell functions are maintained. Also provided are a cell culture including a cell and a peptide hydrogel obtained by the above-described cultivation method, a bioreactor including the cell culture, and a cell preparation including the cell culture.

3 Claims, 24 Drawing Sheets

(56) References Cited

OTHER PUBLICATIONS

Lodish, Harvey. Molecular Cell Biology. New York: W. H. Freeman, 2003, Integrating Cells into Tissues. pp. 197 and 240.

Matsumoto, et al. "Effect of the Two-Layer (University of Wisconsin Solution-Perfluorochemical Plus 02) Method of Pancreas Preservation on Human Islet Isolation, as Assessed by the Edmonton Isolation Protocol", Transplantation 74 (10), 2002, 1414-1419.

* cited by examiner

FIG. 1
(a)
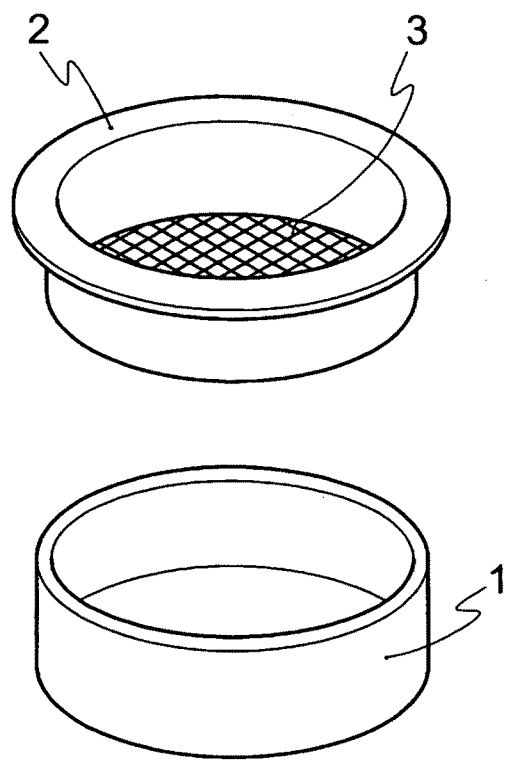
(b)
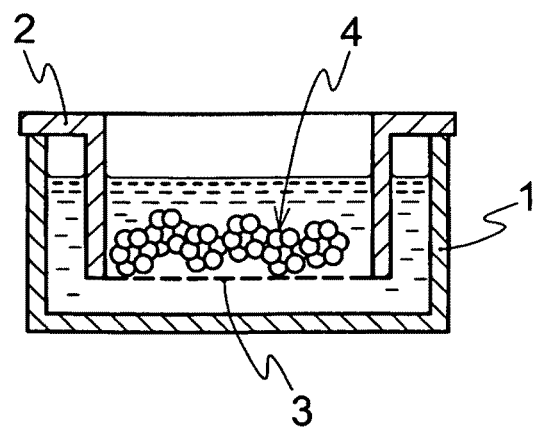

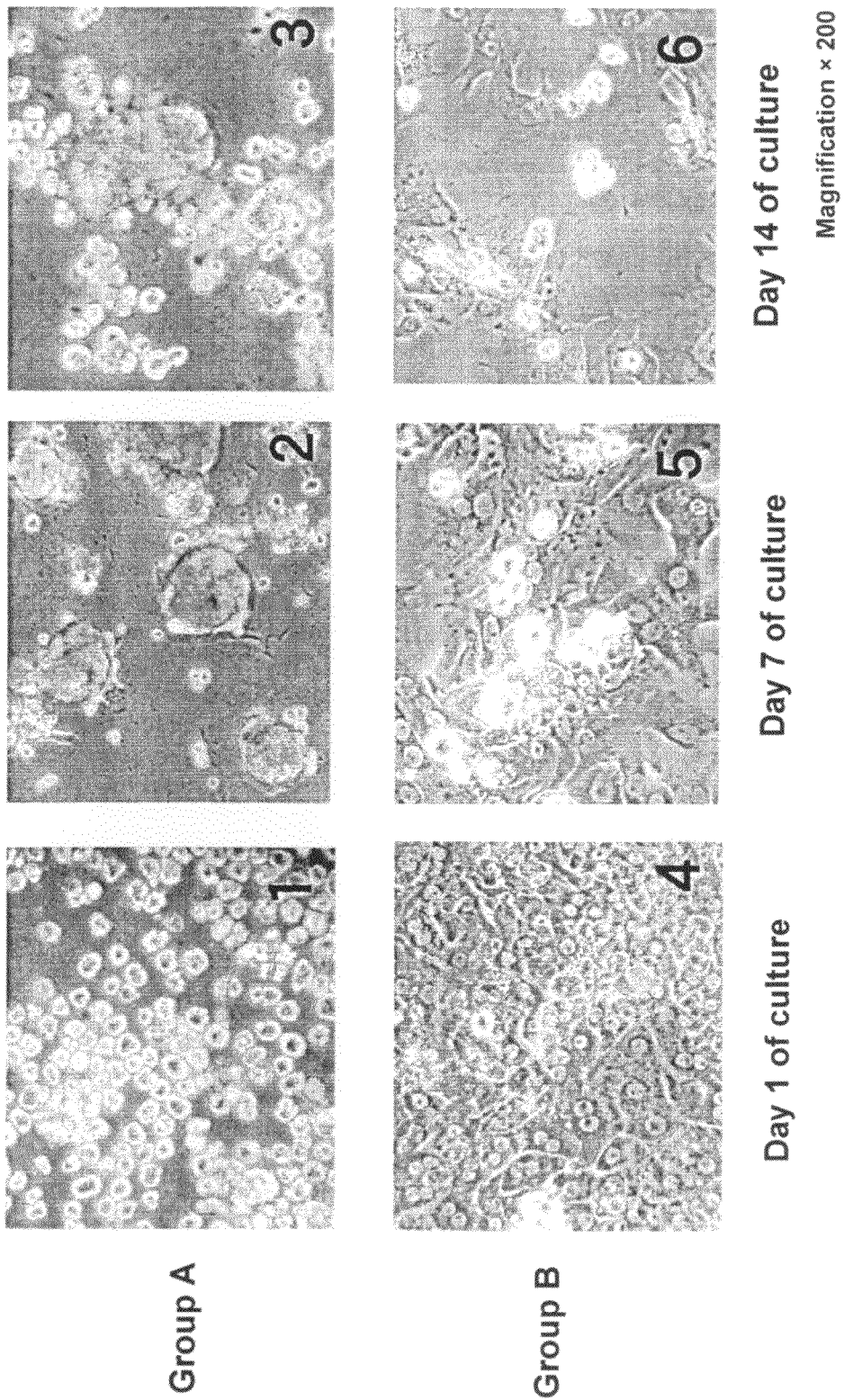

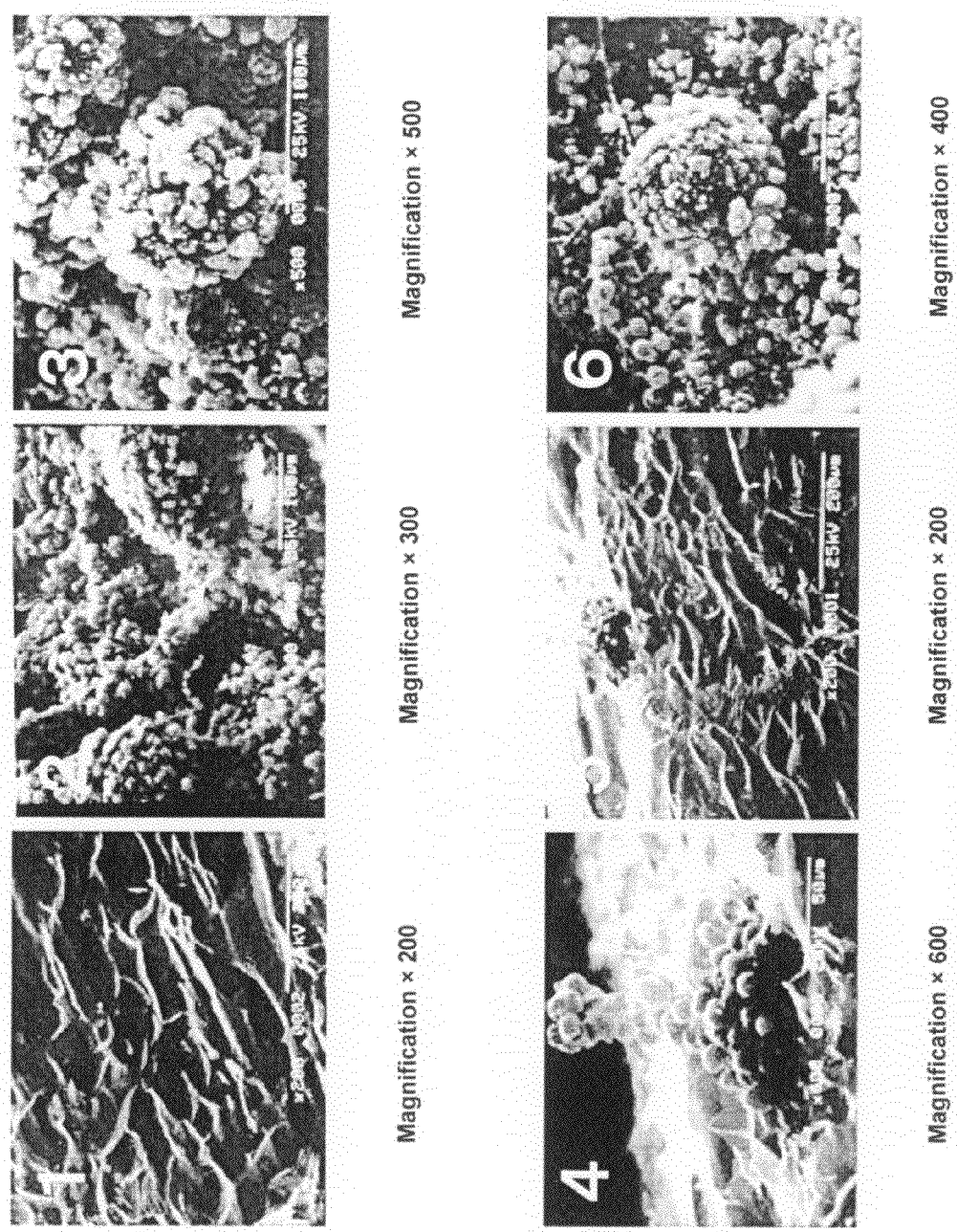

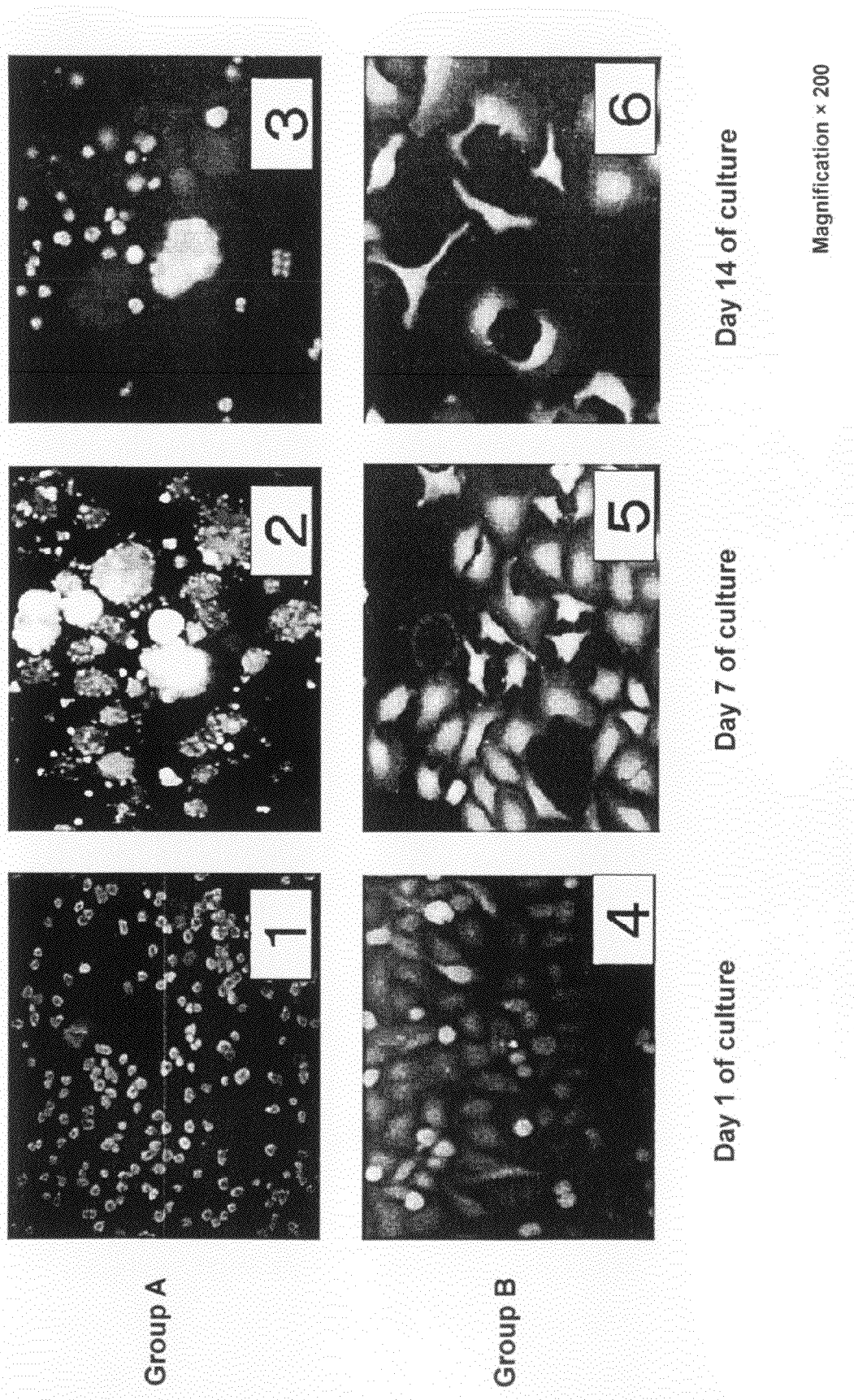

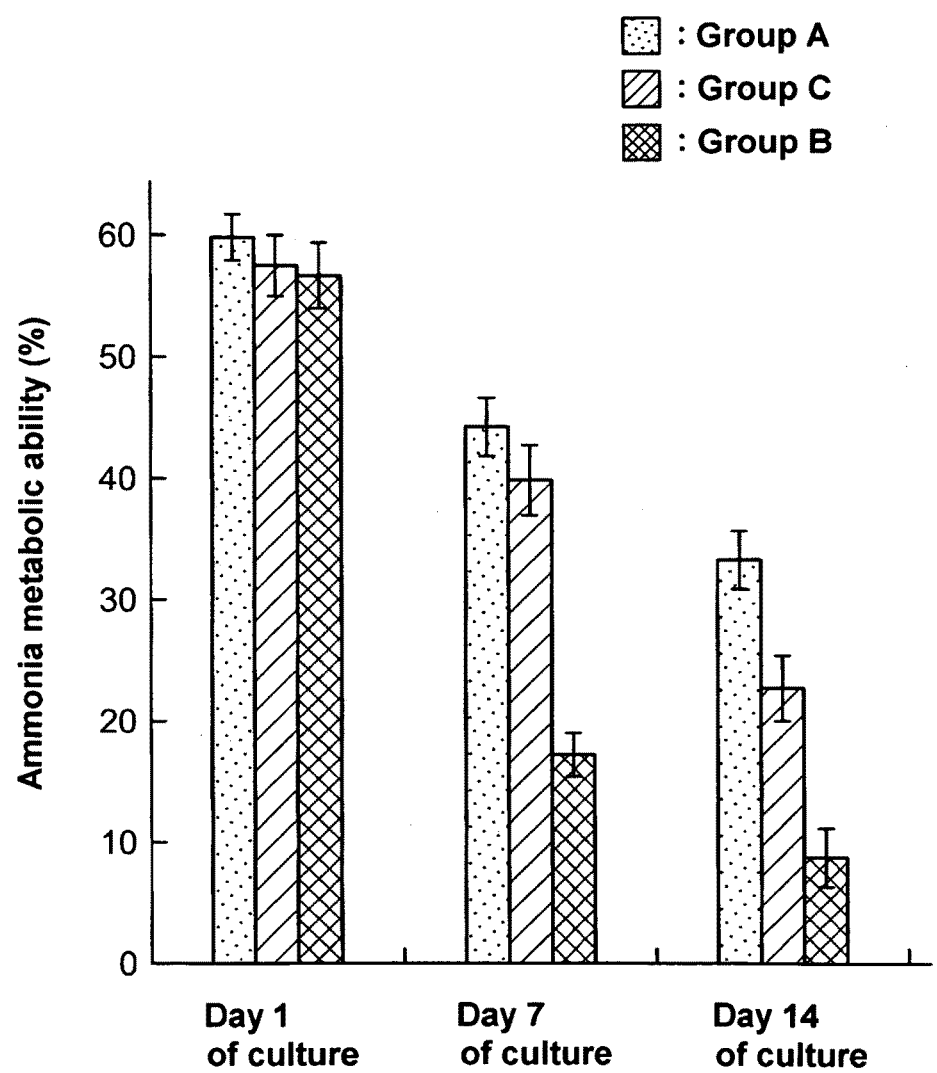

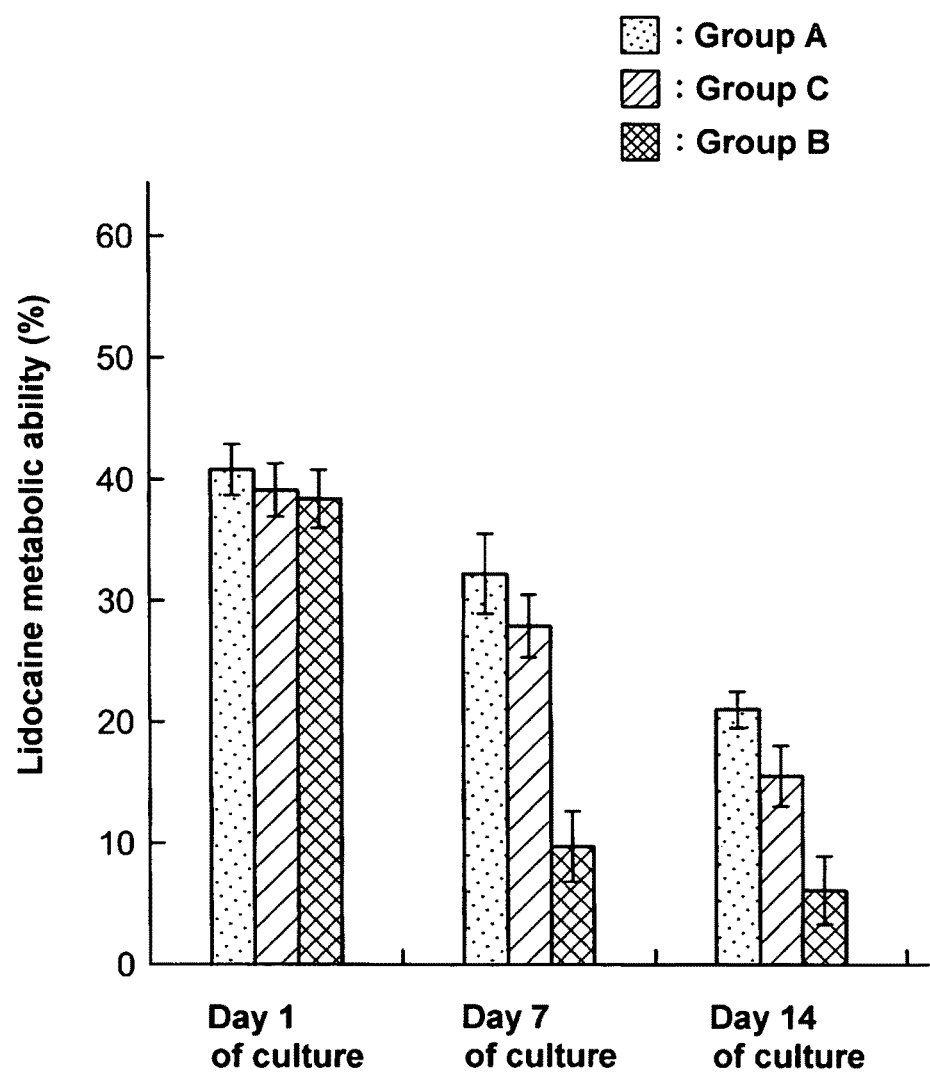

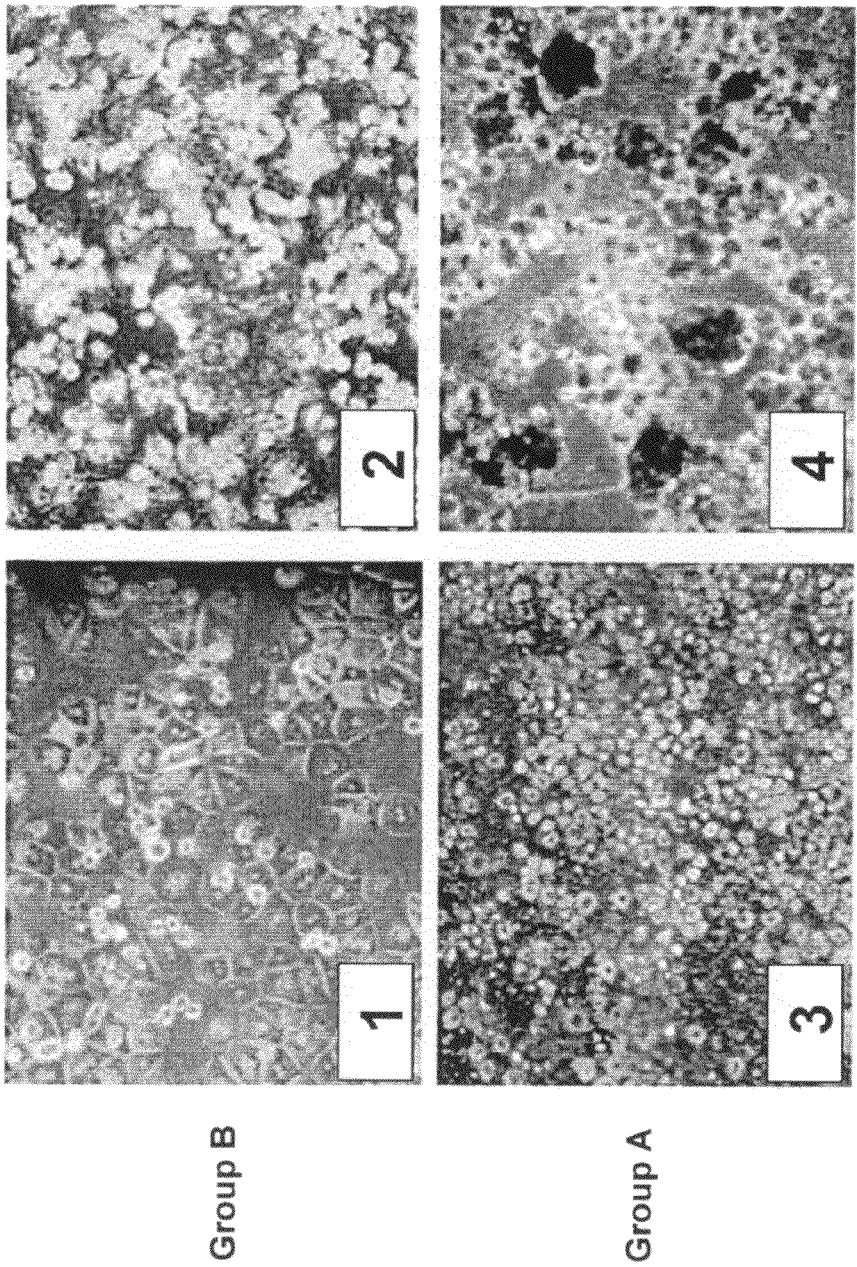

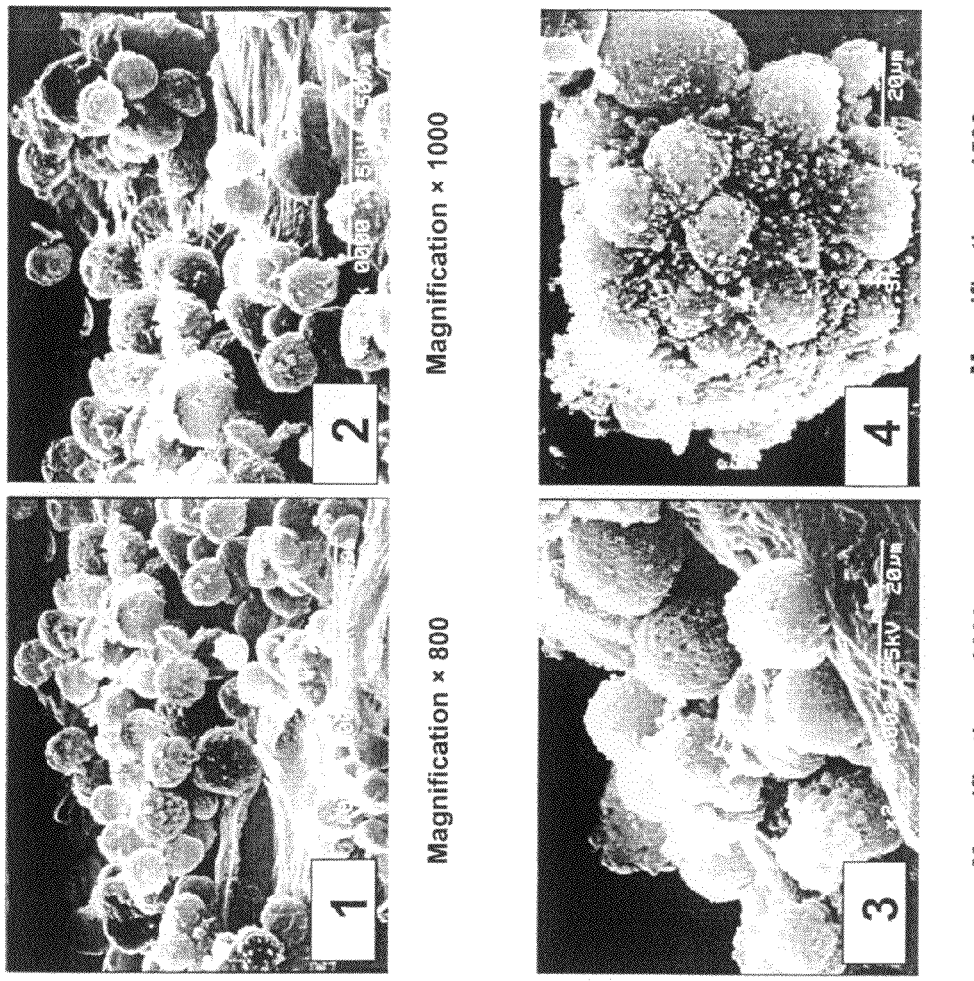

FIG. 9
| Group A | Group B |
|---|---|
| 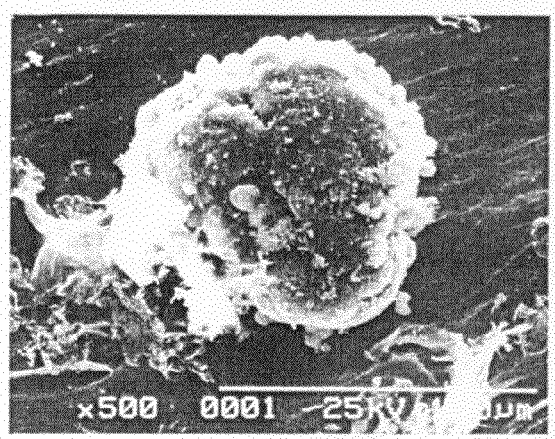 | 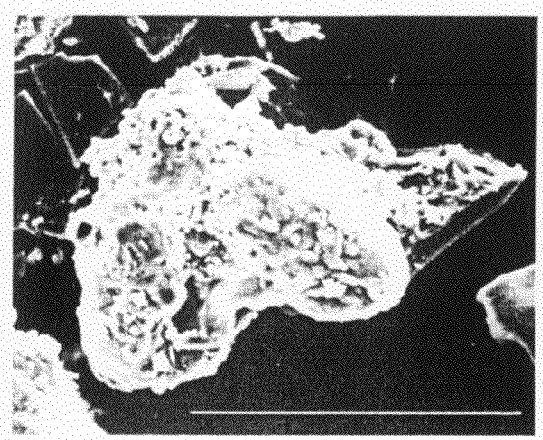 |
| Day 5 of culture | Day 5 of culture |

FIG. 10
(a)
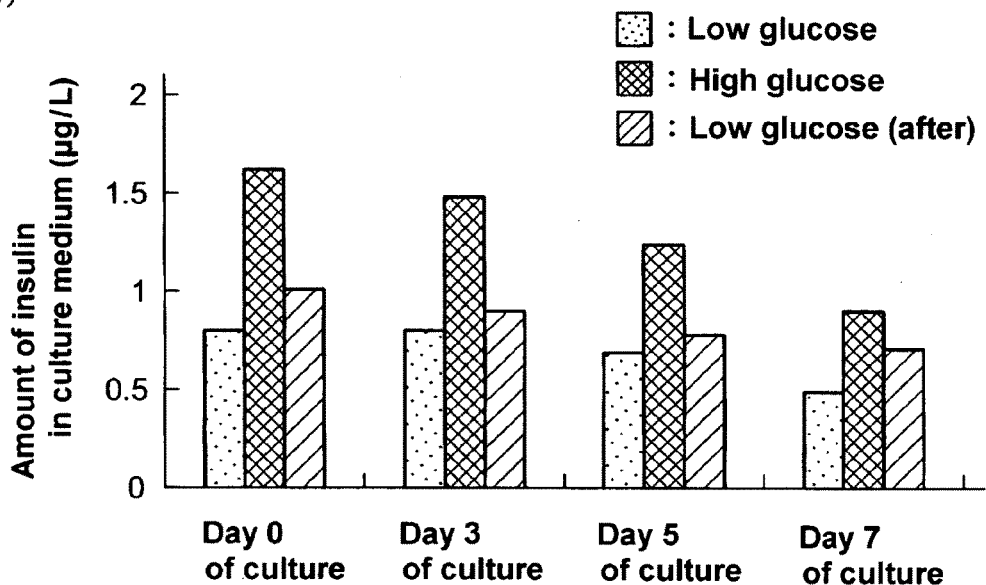
(b)
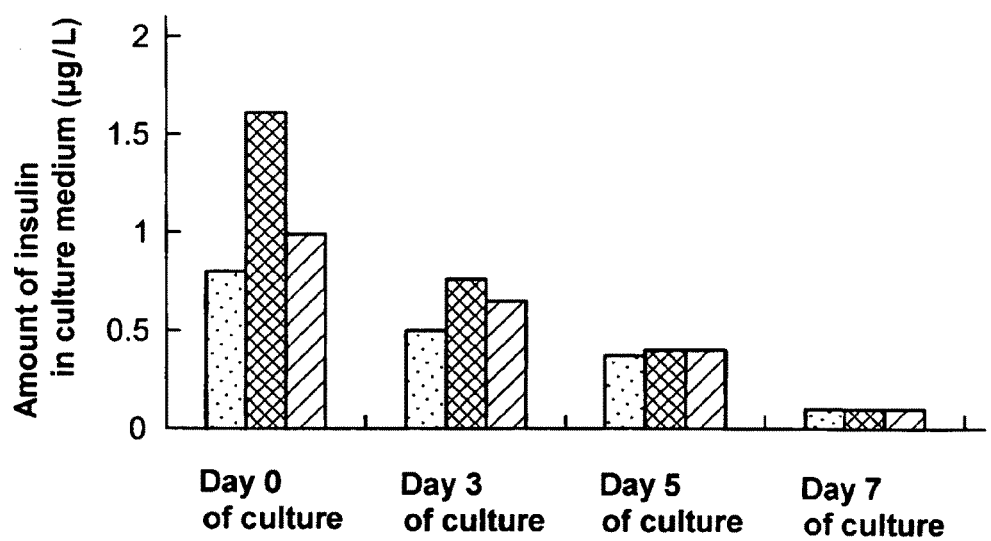

FIG. 11
Group A
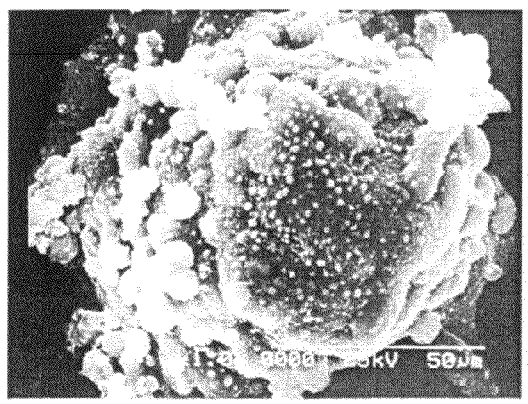
Day 5 of culture
Group B
Day 5 of culture

FIG. 12
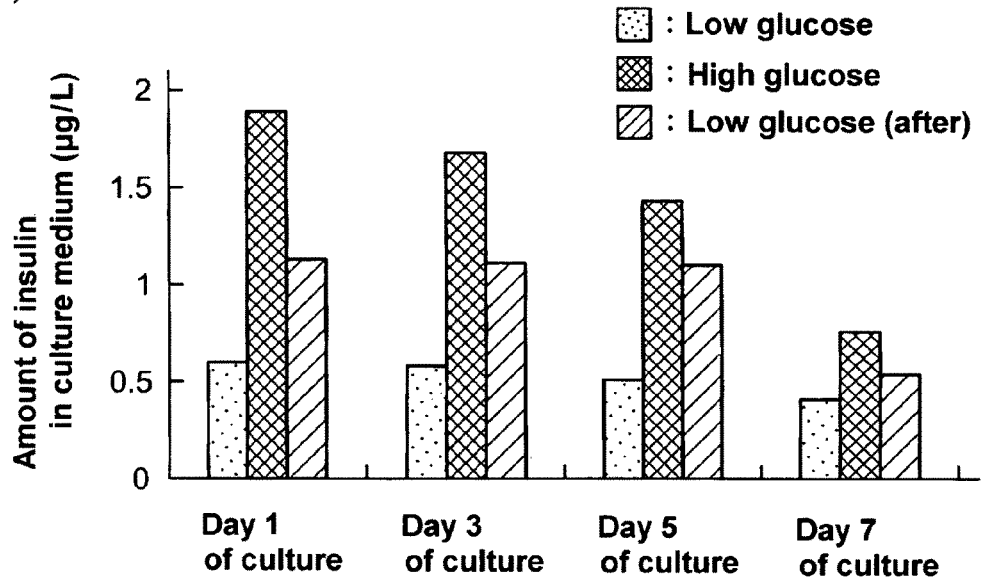
(a)
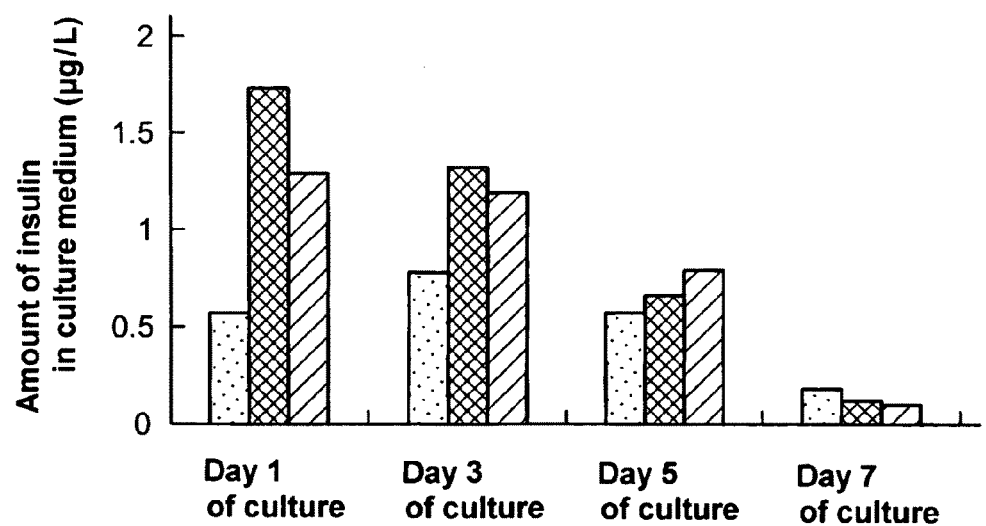
(b)

FIG. 13
(a)
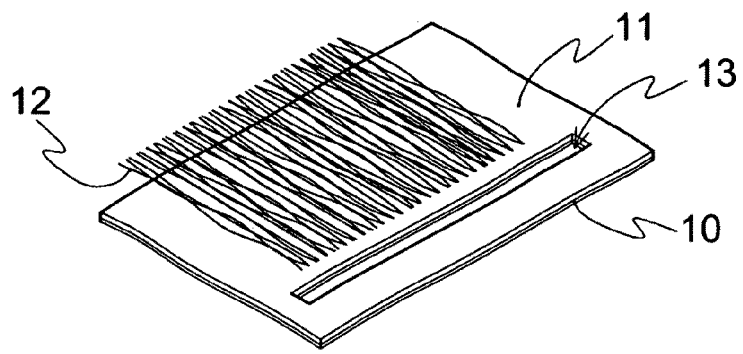
(b)
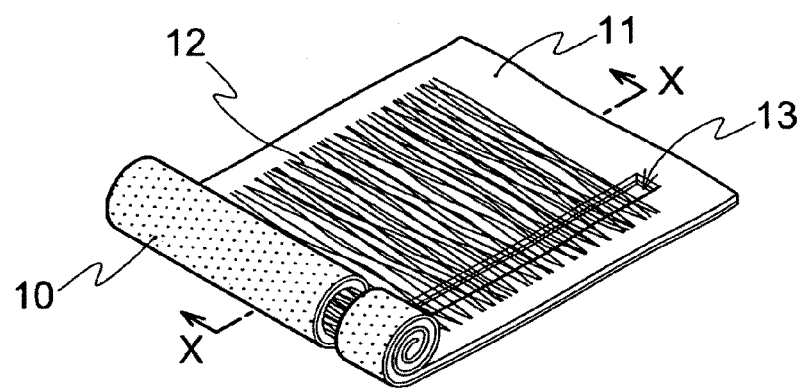
(c)
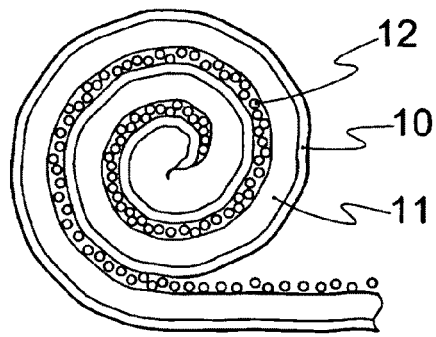
(d)
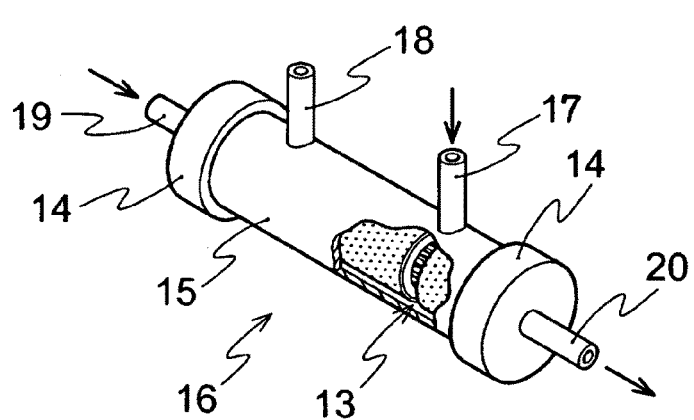

```
SEQUENCE LISTING

<160> NUMBER OF SEQ ID NOS: 3

<210> SEQ ID NO 1
<211> LENGTH: 16
<212> TYPE: PRT
<213> ORGANISM: Artificial
<220> FEATURE:
<223> OTHER INFORMATION: PuraMatrix

<400> SEQUENCE: 1

Arg Ala Asp Ala Arg Ala Asp Ala Arg Ala Asp Ala Arg Ala Asp Ala
1               5                   10                  15

<210> SEQ ID NO 2
<211> LENGTH: 16
<212> TYPE: PRT
<213> ORGANISM: Artificial
<220> FEATURE:
<223> OTHER INFORMATION: EAK16

<400> SEQUENCE: 2

Ala Glu Ala Glu Ala Lys Ala Lys Ala Glu Ala Glu Ala Lys Ala Lys
1               5                   10                  15

<210> SEQ ID NO 3
<211> LENGTH: 16
<212> TYPE: PRT
<213> ORGANISM: Artificial
<220> FEATURE:
<223> OTHER INFORMATION: RAD16

<400> SEQUENCE: 3

Arg Ala Arg Ala Asp Ala Asp Ala Arg Ala Arg Ala Asp Ala Asp Ala
1               5                   10                  15
```

CELL CULTIVATION METHOD AND CELL CULTURE

TECHNICAL FIELD

The present invention relates to a cell cultivation method and a cell culture.

BACKGROUND ART

Internal organs to be subjected to transplantation include, for example, liver. Liver is the largest parenchymatous organ in a human body. It has various functions such as bilirubin metabolism, drug metabolism, and blood coagulation factor production, typically including metabolisms of carbohydrates, proteins and lipids, playing a very important role in an organism.

Thus, severe hepatic failure is very dangerous for the life of a patient even if it is temporary. On the other hand, if a liver function can be substituted for about one week, due to highly regenerative ability of liver, a patient with liver damage caused by fulminant liver failure recovers. For such a serious liver disease, hepatic transplantation is the most effective therapy. However, not all the patient can receive its favor due to serious donor shortage. Under the current actual conditions in Japan, although the life-saving rate has been raised to some extent by a combination of continuous filtration dialysis and plasma exchange as the means for temporarily substituting a liver function, the rate is still insufficient (see, Abe, et al., "Study of plasma exchange for liver failure: beneficial and harmful effects.", The Apher Dial, 2004, 8, p. 180-184), and the establishment of more effective treatment methods have been eagerly desired.

Under such circumstances, therapeutic artificial livers are highly expected, especially, development of bioartificial livers filled with cells in order to utilize a metabolic ability and a protein synthesis ability of living cells is attracting attention. A bioartificial liver is a module prepared by incorporating and fixing hepatocytes in carriers, and it can be said as an artificial liver device simulating liver in human body. The blood in a subject is introduced in the device and the removal of harmful substances in the blood and the feed of biologically active substances such as coagulation factor derived from the liver cells can be carried out by utilizing the metabolizing ability of hepatocytes.

In one example of the experiments of human hepatocytes culturing by the present inventors, the donor was a white male (56 years old) who had experienced head trauma by a traffic accident and the cause of his death was subarachnoid hemorrhage. The transport time from US was about 39 hours. Hepatocytes were separated by normograde perfusion using a collagenase and then, cold-preserved in William's Medium E, and air-transported from Chiba prefecture to Okayama prefecture. The hepatocytes were cultured in culture medium comprising mainly William's Medium E to which deleted form hepatocyte growth factor (dHGF) was added at various concentrations of 0 ng/ml for group A), 10 ng/ml for group B), 100 ng/ml for group C) and 1000 ng/ml for group D), and the effects of dHGF were assessed based on a growth ability by the MIT assay; metabolic abilities of ammonia, lidocaine and diazepam, and an albumin production ability.

In the dHGF-added groups, cell growth was significantly better. Metabolic abilities of ammonia, lidocaine and diazepam and an albumin production ability were significantly better in the groups B) and C), while in the group D), 1000 ng/ml dHGF addition, a drug metabolic ability and an ammonia production ability per given cell number lowered. Visual observation also showed that a cobblestone morphology of hepatocytes was maintained well in the groups B) and C).

In Europe and the United States, hepatocytes are separated from the liver unsuitable for transplantation, and adopted clinically to hepatocyte transplantation and bioartificial livers. However, in Japan, the liver unsuitable for transplantation is prescribed as incineration and thus, it cannot be used for the bioartificial livers. Therefore, a donor liver judged to be unsuitable for transplantation (because of reasons such as fatty liver and intense fibrosis) in the United States was obtained from National Disease Research Interchange (NDR1) via HUMAN & ANIMAL BRIDGING RESEARCH ORGANIZATION laboratory (Ichikawa city, Chiba prefecture, responsible person: Dr. Satoshi Suzuki) in the form of liver block (130 g) which was then separated into liver cells, and a functional cultivation method thereof was investigated. It is extremely important to develop a cultivation method aiming at functional maintenance of human hepatocytes separated from such donor liver unsuitable for transplantation that is only usable resource.

As a countermeasure for the problem wherein use of healthy human hepatocytes is impossible, there have been trials of induction into hepatocytes from human peripheral blood stem cells, myeloid stem cells and liver precursor cells. These cells, however, show poor growth ability and thus, it is not realistic to obtain sufficient number of cells necessary for application to bioartificial livers (at least one billion). Therefore, in Europe and China, clinical trials of bioartificial livers using porcine hepatocytes have been carried out in humans (see, van de Kerkhove, et al., "Phase I clinical trial with the AMC-bioartificial liver.", Academic Medical Center Int J Artif Organs, 2002, 25, p. 950-959, Donini, et al., "Temporary neurological improvement in a patient with acute or chronic liver failure treated with a bioartificial liver device", Am J Gastroentrol, 2000, 95, p. 1102-1104, Mazariegos, et al., "Safety observations in phase I clinical evaluation of the Excorp Medical Bioartificial Liver Support System after the first four patients.", ASAIO J, 2001, 47, p. 471-475, Ding, et al., "The development of a new bioartificial liver and its application in 12 acute liver failure patients.", World J Gastroenterol, 2003, 9, p. 829-832, Demetriou, et al., "Prospective, randomized, multicenter, controlled trial of a bioartificial liver in treating acute liver failure.", Ann Surgery, 2004, 239, p. 660-670, Mundt, "A method to assess biochemical activity of liver cells during clinical application of extracorporeal hybrid liver support.", Int J Artif Organs, 2002, 25, p. 542-548, Morsiani, et al., "Early experiences with a porcine hepatocyte-based bioartificial liver in acute hepatic failure patients.", Int J Artif Organs, 2002, 25, p. 192-202, Xue, et al., "TECA hybrid artificial liver support system in treatment of acute liver failure.", World J Gastroenterol, 2001, 7, p. 826-829).

It is expected that cell or tissue culture technologies can be adopted industrially for regenerative medicine, cell preparation, useful substance production (bioreactor), investigation and research into function of tissue, organ and internal organ, screening of new drugs, animal experiment substitute methods for evaluating influences of endocrine disrupting chemicals, and cell chips, typically including cell transplantation and bioartificial organs.

Conventionally, as a method for culturing animal cells having adhesiveness, a two-dimensional cultivation method, that is, a so-called monolayer cultivation method has been generally used, in which a substrate such as a culture dish made of polystyrene or glass is used and the surface thereof is coated with a living body-derived factor, or treated chemically or physicochemically, and cells are adhered to and spread on the surface. For example, if cells are cultured on a polystyrene dish coated with collagen, an animal-derived intercellular matrix component, or on a polystyrene dish having a surface hydrophilized by plasma treatment, the cells adhere to and spread on the surface, thereby taking a cell morphology in which cytoplasm is spread in flat form.

On the other hand, cells isolated from tissue and internal organs of organisms, so-called primary cells, often maintain properties and functions of tissue and internal organs from which the cells are originated and thus, these cells have a great deal of potential in industrial application. However, it is known that in the monolayer cultivation method, properties and functions of various cells will be lost in several days or several weeks, in most cases. Particularly, in the case of primary hepatocytes which are well-differentiated and have various complicated functions among primary cells, properties and functions thereof tend to be lost quickly in the monolayer culture. For example, it is known that if hepatocytes isolated from rat liver are monolayer-cultured, important functions of liver, that is, a protein synthesis function, a detoxification function and a drug metabolic function are lowered or lost within several days from initiation of culture. It is hypothesized that in a monolayer cultivation method, cells have cytoplasm in the form of flat two-dimensional state and thus, mechanisms originally possessed by cells in a living body, such as an intracellular structure, polarity, and information exchange due to bonding with adjacent cells, are lowered and lost, causing lowering and loss of properties and functions originally possessed by cells (see, Japanese Unexamined Patent Publication No. 128660/2001).

In order to avoid such lowering and loss of the properties and functions originally possessed by cells, a so-called "three-dimensional cultivation method" has drawn attention in which cells are mutually assembled to construct a three-dimensional structure similar to living tissue. Scaffolds in such a three-dimensional cultivation method are roughly classified into two types. One is an animal-derived intercellular matrix component, and another is a synthetic polymer. Examples of the animal-derived intercellular matrix component include collagen gel, laminin, and animal basement membrane-derived component (trade name: Matrigel, available from Becton Dickinson and Company (constituents: laminin 56%, collagen IV 31% and entactin 8%)). It is reported that when, for example, rat hepatocytes are cultured with Matrigel, spheroid is formed (see, Bissell, et al., "Transcriptional regulation of the albumin gene in cultured rat hepatocytes. Role of basement-membrane matrix.", Mol Biol Med, 1990, 7, p. 187-197). Examples of the synthetic polymer include polyglucosic acid and poly L-lactic acid. It is reported that when, for example, rat hepatocytes are cultured with polyglucosic acid, spheroid is formed (see, Fiegel, et al., "Influence of flow conditions and matrix coatings on growth and differentiation of three-dimensionally cultured rat hepatocytes.", Tissue Eng, 2004, 10, p. 165-174).

Since cells cultured by the three-dimensional cultivation method are capable of maintaining properties and functions originally possessed by cells at higher level for a longer period of time as compared with cells cultured by a two-dimensional cultivation method, as described above, it is anticipated that the cells cultured by a three-dimensional cultivation method can be highly effective means for industrial applications such as bioartificial organs, regeneration medicine, cell preparation, useful substance production (bioreactor), investigation and research of function of tissue, organ and internal organ, screening of new drugs, animal experiment substitute methods for evaluating influences of endocrine disrupting chemicals, and cell chips.

DISCLOSURE OF INVENTION

However, the above-described scaffolds in the three-dimensional cultivation method had the following issues. That is, when an animal-derived intercellular matrix component is used as a scaffold, reproducibility is poor due to a large variability between lots. Furthermore, there is a possibility of contamination with unknown factors such as unknown viruses, and a fear of infection in clinical use. When a synthetic polymer is used as a scaffold, the fiber diameter is as large as 10 to 50 μm and thus, the environment is substantially the same as in flat culture when taking the size of cells (5 to 20 μm) into consideration. Additionally, since inter-fiber size (pore size) is as large as 10 to 200 μm, there is a problem that intercellular matrix components produced by cells do not remain in the scaffold, and suspend into culture medium. Furthermore, there is a problem that the components remain in a body as extraneous materials in case of transplantation, because of low biodegradability.

In view of the above-described issues, an objective of the present invention is to provide a technology in order to perform high-dimensional culture for a long period of time for cells such as porcine hepatocyte, human hepatocyte, porcine pancreatic islet and human pancreatic islet, under conditions where cell survival, cell morphology and cell functions are maintained.

As a result of intense study for achieving the above-described objective, it has been found that the above-described objective can be attained by culturing a cell using a peptide hydrogel having the same fiber size and pore size as those of natural intercellular matrices, and having biocompatibility and biodegradability, leading to completion of the present invention as a scaffold.

That is, the present invention relates to a method for culturing a cell wherein the cell is cultured using a peptide hydrogel as a scaffold.

In a preferable embodiment of the present invention, the cell is cultured further using an insert.

In a further preferable embodiment of the present invention, the above-described cell is at least one member selected from the group consisting of porcine hepatocyte, human hepatocyte, porcine pancreatic islet and human pancreatic islet.

The present invention also relates to a cell culture comprising a cell and a peptide hydrogel obtained by the above-described cultivation method.

In a preferable embodiment of the present invention, cells in the above-described culture constitute a cell culture having a spheroid morphology.

In a further preferable embodiment of the present invention, cells in the above-described culture are hepatocytes having formation of a cell adhesion apparatus and/or bile canaliculi.

In a further preferable embodiment of the present invention, cells in the above-described culture constitute a pancreatic islet showing at least 12 points in the sum of evaluation values regarding pancreatic islet morphological criteria: shape, border shape, cell integrity and cell diameter and in which the ratio of insulin secretion in low glucose concentration to that in high glucose concentration to glucose stimulation is at least 1.5-fold.

The present invention also relates to a bioreactor including a cell culture obtained by culturing hepatocyte using a peptide hydrogel as a scaffold.

In a preferable embodiment of the present invention, the above-described bioreactor metabolizes ammonia, diazepam or lidocaine.

The present invention also relates to a bioreactor including a cell culture obtained by culturing pancreatic islet using a peptide hydrogel as a scaffold.

In a preferable embodiment of the present invention, the above-described bioreactor produces insulin.

The present invention further relates to a cell preparation including a cell culture obtained by culturing cells using a peptide hydrogel as a scaffold.

BRIEF DESCRIPTION OF DRAWINGS

FIG. 1(a) is a schematic drawing showing one example of a culture vessel used in a cultivation method of the present invention using a peptide hydrogel as a scaffold. Numerical reference 1 shows a culture dish, and numerical reference 2 shows an insert. A filter 3 is provided at the bottom of the insert 2. The insert 2 is inserted in the culture dish 1. A peptide hydrogel is spread on the filter 3 of the insert 2, and a cell is placed thereon and cultured. FIG. 1(b) is a cross-sectional drawing showing one embodiment of a cultivation method of the present invention using the culture vessel shown in FIG. 1(a). Numerical reference 4 shows a cell. The peptide hydrogel is not illustrated.

FIG. 2(a) is a phase-contrast microscopy image showing culture conditions of porcine hepatocytes cultured by a cultivation method of the present invention using a peptide hydrogel as a scaffold (Photographs 1, 2 and 3) and porcine hepatocytes cultured by a conventional cultivation method using collagen as a scaffold (Photographs 4, 5 and 6).

FIG. 2(b) is a scanning electron microscopy image showing culture conditions of porcine hepatocytes cultured by a cultivation method of the present invention using a peptide hydrogel as a scaffold (Photographs 1, 2 and 3) and porcine hepatocytes cultured by a conventional cultivation method using collagen as a scaffold (Photographs 4, 5 and 6).

FIG. 3 is a phase-contrast microscopy image showing a viability status of porcine hepatocyte cultured by a cultivation method of the present invention using a peptide hydrogel as a scaffold (Photographs 1, 2 and 3) and porcine hepatocyte cultured by a conventional cultivation method using collagen as a scaffold (Photographs 4, 5 and 6).

FIG. 4(b) is a graph comparing metabolic abilities of ammonia of porcine hepatocyte cultured by a cultivation method of the present invention using a peptide hydrogel as a scaffold (group A), porcine hepatocyte cultured by a conventional cultivation method using collagen as a scaffold (group B) and porcine hepatocyte cultured by a cultivation method using Matrigel as a scaffold (group C).

FIG. 5(b) is a graph comparing metabolic abilities of lidocaine in porcine hepatocyte cultured by a cultivation method of the present invention using a peptide hydrogel as a scaffold (group A), porcine hepatocyte cultured by a conventional cultivation method using collagen as a scaffold (group B) and porcine hepatocyte cultured by a cultivation method using Matrigel as a scaffold (group C).

FIG. 7(a) is a phase-contrast microscopy image showing culture conditions of human hepatocyte cultured by a cultivation method of the present invention using a peptide hydrogel as a scaffold (Photographs 1, 2 and 3) and human hepatocyte cultured by a conventional cultivation method using collagen as a scaffold (Photographs 4, 5 and 6).

FIG. 7(b) is a scanning electron microscopy image showing culture conditions of human hepatocyte cultured by a cultivation method of the present invention using a peptide hydrogel as a scaffold (Photographs 1, 2 and 3) and human hepatocyte cultured by a conventional cultivation method using collagen as a scaffold (Photographs 4, 5 and 6).

FIG. 9 is a scanning electron microscopy image showing culture conditions of porcine pancreatic islet cultured by a cultivation method of the present invention using a peptide hydrogel as a scaffold (group A) and porcine pancreatic islet cultured by a conventional cultivation method using collagen as a scaffold (group B).

FIG. 10(a) is a graph showing the insulin production ability of porcine pancreatic islet cultured by a cultivation method of the present invention using a peptide hydrogel as a scaffold (group A) and FIG. 10(b) is a graph showing the insulin production ability of porcine pancreatic islet cultured by a conventional cultivation method using collagen as a scaffold (group B).

FIG. 11 is a scanning electron microscopy image showing culture conditions of porcine pancreatic islet cultured by a cultivation method of the present invention using a peptide hydrogel as a scaffold (group A) and porcine pancreatic islet cultured by a conventional cultivation method using collagen as a scaffold (group B).

FIG. 12(a) is a graph showing the insulin production ability of human pancreatic islet cultured by a cultivation method of the present invention using a peptide hydrogel as a scaffold (group A) and FIG. 12(b) is a graph showing the insulin production ability of human pancreatic islet cultured by a conventional cultivation method using collagen as a scaffold (group B).

FIG. 13 is a drawing showing manufacturing processes in turn using one embodiment of a bioreactor of the present invention as an example. (a) is a schematic drawing showing the condition of hollow fibers 12 arranged on nonwoven fabric 11 equipped with lining 10. Here, the nonwoven fabric 11 equipped with lining 10 has a slit 13. (b) is a schematic drawing showing a process of winding the material in a form of sheet shown in (a) in the form of roll. (c) is an X-X line cross-section enlarged drawing of (b). (d) is a schematic drawing showing a bioreactor 16 which can be utilized in a bioartificial liver having a roll composed of the hollow fibers 12 and the nonwoven fabric 11 incorporated in a cylindrical vessel 15 equipped with liquid leak prevention parts 14 on both ends. The bioreactor 16 is equipped with a cell injection port 17 and a discharge port 18 by which a cell sample can be collected, and the slit 13 is disposed so as to communicate with the cell injection port 17.

BEST MODE FOR CARRYING OUT THE INVENTION

Figure 2C:
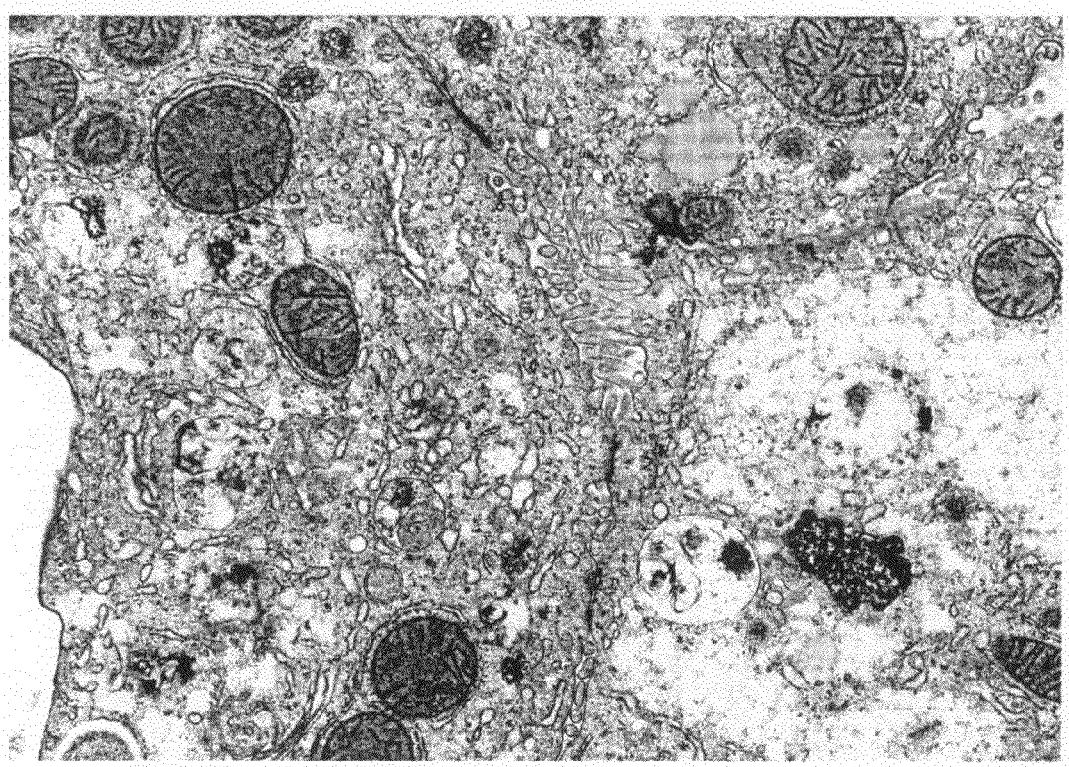
FIG. 2(c) is a transmission electron microscopy image showing the cross-section of porcine hepatocyte cultured using an insert in a cultivation method of the present invention using a peptide hydrogel as a scaffold, showing that the porcine hepatocyte constitutes a high-dimensional culture. Between cells, a cell adhesion apparatus and bile canaliculi are formed.

A cell used as subject matters in the present invention includes, for example, hepatocyte of mammals such as porcine, monkey, anthropoid and human or pancreatic islet of mammals such as porcine, monkey, anthropoid and human. Among these, preferable is at least one member selected from the group consisting of porcine hepatocyte, human hepatocyte, porcine pancreatic islet and human pancreatic islet.

In the present invention, a self-assembling peptide hydrogel is adopted as the scaffold to be used in performing high-dimensional culture of cells such as porcine hepatocyte, human hepatocyte, porcine pancreatic islet and human pancreatic islet. As the peptide hydrogel, PuraMatrix of SEQ ID NO:1 (Ac-(RADA)$_4$-CONH$_2$), EAK16 of SEQ ID NO:2 (Ac-AEAEAKAKAEAEAKAK-CONH$_2$) and RAD 16 of SEQ ID NO: 3 (Ac-RARADADARARADADA-CONH$_2$) are mentioned, and among them, PuraMatrix of SEQ ID NO:1 commercially available from Three D Matrix Japan K. K. is preferably mentioned.

Also, self-assembling peptides having an amino acid sequence and amino acid residue number different from those of PuraMatrix of SEQ ID NO:1 can be used as the scaffold. As preferable amino acid sequences, repetitions of X—N—Y—N (X represents a basic amino acid such as arginine and lysine, N represents a neutral amino acid such as alanine and glycine, Y represents an acidic amino acid such as aspartic acid and glutamic acid) are mentioned.

Since self-assembling peptides such as PuraMatrix of SEQ ID NO:1 have the peptide sequences with no obvious physiologically active motif, there is no fear of deterioration of original cell functions. A physiologically active motif is correlated with control of many intracellular phenomena such as transcription and thus, if a physiologically active motif is present, proteins in cytoplasm and on cell surface are phosphorylated by an enzyme recognizing this motif. If a physiologically active motif is present in a scaffold, there is a possibility of suppression of transcription activating ability of various functional proteins. For example, in a hepatocyte, side effects such as suppression of an albumin production ability and drug metabolic ability can occur. In self-assembling peptides such as PuraMatrix of SEQ ID NO:1 having no physiologically active motif, such a fear does not exist. Therefore, self-assembling peptides such as PuraMatrix of SEQ ID NO:1 are scaffolds suitable for cell culture functioning only as a physical cell foothold.

PuraMatrix of SEQ ID NO:1 is an oligo peptide containing 16 amino acid residues (Ac-(RADA)$_4$-CONH$_2$) and having a length of about 5 nm, and its solution is in liquid form when pH is lower than 5.0, when pH is changed to values of at least 5.0, self-assembly of peptide occurs, forming nano fibers having a diameter of about 10 nm. As a result, the peptide solution will be gelated.

The above-described nano fibers have a diameter of 10 to 20 nm and a pore size of 5 to 200 nm, on average. Since the range of these numerical value is approximately the same as those of collagen, a natural intercellular matrix, self-assembling peptides are the suitable scaffold for cell culture.

PuraMatrix of SEQ ID NO:1 is an amphiphilic peptide having an amino acid sequence in which residues of positively charged arginine, negatively charged aspartic acid and hydrophobic alanine repeat alternately, and self-assembly of peptide is ascribable to an ionic bond and a hydrophobic bond between the peptide molecules by amino acids comprising the peptide.

Self-assembly conditions of a self-assembling peptide include physiological pH and a salt concentration. In particular, monovalent alkali metal ions are important, i.e., sodium ions and potassium ions present in large amount in an organism contribute to promotion of gelation. Once gelled, the gel does not degrade even if usual protein degeneration conditions, for example, high temperature, and degenerants such as acid, alkali, protease, urea and guanidine hydrochloride, are used.

This self-assembling peptide is capable of easily forming a three-dimensional porous scaffold, which is difficult to achieve with the other technologies. The density and the average pore size of the nano fiber correlates to the concentration of the peptide solution adopted. Depending on the concentration of an aqueous solution of a self-assembling peptide, the strength of the gel varies, and culture conditions suitable for culturing cells can be obtained. It is therefore possible to encapsulate cell within a three-dimensional environment, or to differentiate and grow cell successfully on the surface of a peptide hydrogel (see, Zhang, et al., Biomaterials, December; 16 (18): 1385-93, 1995, Holmes, et al., Proc Natl Acad Sci USA. June 6; 97(12): 6728-33, 2000, and Kisiday, et al., Proc Natl Acad Sci USA. July 23; 99(15): 9996-10001, 2002).

Thus, a self-assembling peptide is capable of providing effects equivalent to or more than those with animal-derived extracellular matrices such as collagen, fibronectin and mouse sarcoma extracellular matrix, in cell culture technologies. Furthermore, since a self-assembling peptide is produced through chemical synthesis, it does not include unknown components ascribable to animal-derived extracellular matrices. This nature causes no fear of infections including BSE, also showing high safety for medical treatments.

A self-assembling peptide comprising natural amino acids is also excellent in terms of its biocompatibility and degradability in the living body. Thus, it is reported that when PuraMatrix of SEQ ID NO:1 is injected into mouse myocardium, for example, cells penetrate into the injected PuraMatrix of SEQ ID NO:1 and normal tissue is formed. Although the degradation time varies depending on conditions such as injection place, fibers are degraded and discharged in about 2 to 8 weeks after injection.

Cell used as subject matters in the present invention includes cell collected from human and animal or commercially available cell. Specifically mentioned are porcine hepatocyte, human hepatocyte, porcine pancreatic islet and human pancreatic islet.

Liver cells are used in the present invention can be obtained by a method of excision from animal such as porcine and a method of using human donor liver, as well as obtaining those commercially available (for example, Sanko Junyaku Co. Ltd., and Dainippon Seiyaku K. K.).

Porcine or human pancreatic islet that is used in the present invention can be isolated from porcine or human pancreas according to known methods (see, Staudacher C, Ricordi C, Stella M, SOcci C, Cammelli L, Ferrari G, Dicarlo V., Minerva Chir. 31: 1665-1668, 1985, Ricordi C, Finke E H, Lacy P E., Diabetes 35: 649-653, 1986, and Lakey J R T, Kobayashi N, Shapiro A M J, Ricordi C, Okitsu T: Current human islet isolation protocol. Medical Review Co., Ltd., Osaka, Japan, 2004).

As the cell cultivation method and culture conditions, common cultivation methods and conditions can be adopted depending on the type of cell. For example, the cultivation method includes coculture in which a mixture of PuraMatrix of SEQ ID NO:1 and a cell is cultured in culture medium, and preferable is culture with an insert (also referred to as culture insert) from the viewpoint of avoiding a risk of direct contact of culture medium to PuraMatrix of SEQ ID NO:1 to impart a damage to PuraMatrix of SEQ ID NO:1 itself when the culture medium is exchanged to a new one (see, FIGS. 1(*a*) and (*b*)).

An insert 2 is a cell or tissue culture equipment which has a filter 3 (also referred to as membrane) at the bottom and is stacked on a culture dish 1 before seeding a cell on the insert and culturing the cell (see, FIGS. 1(*a*) and (*b*)). Examples of the material of the filter include polyester, polycarbonate, cellulose-mixed ester and polyethylene terephthalate, and the filter pore size is preferably 0.4 to 3.0 μm considering the size of cell. By using the insert, mechanical damage due to culture medium exchange can be reduced. It can also be used for measurement of cell secretion and drug uptake by cell. The insert is commercially available, for example, from Becton Dickinson Biosciences, Corning Life Sciences and Millipore.

In the mixing method of a self-assembling peptide and a cell using an insert, it is preferable in the present invention that a self-assembling peptide and a cell are mixed and then, culture medium is exchanged for new one several times (e.g., 2 to 4 times). This operation exerts an effect of converting low pH (pH 1.0 to 3.0) of a self-assembling peptide into physiological pH (pH 6.0 to 8.0), resulting in secure gelation of the self-assembling peptide. Generation of physiological pH exerts an effect of suppressing damage to cell to minimum. In culture medium exchange, culture medium in an insert is not exchanged, and only culture medium in a culture dish is exchanged. By this strategy, mechanical damage to a self-assembling peptide due to medium exchange can be suppressed to minimum.

The concentrations of a self-assembling peptide and a cell in the cultivation method of the present invention are preferably 0.5 to 1% and $1 \times 10^5$ to $3 \times 10^5$ cells/ml, and most preferably 0.5% and $2 \times 10^5$ cells/ml, respectively.

A medium used in the cell cultivation method of the present invention can be any composition providing it can grow cell, and may advantageously be one containing components necessary for cell culture such as minerals, sugars, amino acids, peptides, vitamins, organic acids, nucleic acids, pH regulators and enzymes.

Examples of the medium for hepatocyte include commercially available media for hepatocyte, William's Medium E (available from SIGMA, St. Louis, Mo.), cell medium kit HCM BulletKit (product code CC-3198) (manufactured by Takara), serum free medium for hepatocyte culture: HapatoZYME-SFM (catalogue number 17705-021) (available from Invitrogen), medium for hepatocyte maintenance (Long-Term Culture Medium) (catalogue numbers HE0306-5, HE0306) (available from KAC Co., Ltd.) and William's Medium E containing fetal bovine serum, of which William's Medium E is preferable in terms of cost.

To the above-described hepatocyte medium, fetal bovine serum, human serum and various cell growth factors are preferably added when growth of cells is taken into consideration. Furthemiore, to the above-described medium, at least one of transferrin, hydrocortisone, ascorbic acid, insulin, glutamine and nicotineamide are preferably added, and it is particularly preferable to add all of these types. The addition concentration is preferably 2.5 to 5.0 μg/ml for transferrin, 5 to 10 μg/ml for hydrocortisone, 1 to 2 mmol/l for ascorbic acid, 2.5 to 5 μg/ml for insulin, 2 to 5 mmol/l for glutamine and 1 to 20 mmol/l for nicotineamide, further preferably 5.0 μg/ml for transferrin, 5 μg/ml for hydrocortisone, 2 mmol/l for ascorbic acid, 5 μg/ml for insulin, 5 mmol/l for glutamine and 10 mmol/l for nicotineamide.

Examples of the pancreatic islet medium include commercially available RPMI-1640 medium (available from SIGMA), William's Medium E (available from SIGMA), CMRL1066 medium (available from Invitrogen), low glucose DMEM (available from GIPCO) and high glucose DMEM (available from GIPCO), and preferable is low glucose DMEM from the viewpoint that since it can suppress insulin secretion from pancreatic islet to protect from exhaustion of pancreatic islet cell.

To the above-described pancreatic islet medium, fetal bovine serum, human serum and various cell growth factors are preferably added when growth of cells is taken into consideration. Furthermore, to the above-described medium, at least one of calcium chloride, glutamine, 2-[4-(2-hydroxyethyl)-1-piperazinyl]ethanesulfonic acid (HEPES), nicotineamide, trasylol, zinc sulfate, troglitazone and exendin-4 are preferably added, and it is particularly preferable to add all of these types. The addition concentration is preferably 1 to 3 mmol/l for calcium chloride, 1 to 3 mmol/l for glutamine, 10 to 30 μmol/l for HEPES, 1 to 20 mmol/l for nicotineamide, 5000 to 20000 IU/l for trasylol, 10 to 20 μmol/l for zinc sulfate, 1 to 20 μmol/l for troglitazone and 2 to 100 nmol/l for exendin-4, further preferably 2.13 mmol/l for calcium chloride, 2 mmol/l for glutamine, 20 μmol/l for HEPES, 10 mmol/l for nicotineamide, 20000 IU/l for trasylol, 16.7 μmol/l for zinc sulfate, 10 μmol/l for troglitazone and 10 nmol/l for exendin-4.

According to the hepatocyte high-dimensional cultivation method of the present invention, physiologically active substances such as serum albumin as a production component and various coagulation factors originally contained in hepatocyte can be produced efficiently by culturing hepatocyte derived from porcine or human. In addition to this, it is possible to provide hepatocyte having a protein production ability, gluconeogenesis ability, urea production ability, blood detoxification and purification ability, and amino acid, sugar and lipid metabolic abilities that are functions of hepatocyte. According to the above-described hepatocyte cultivation method, a detoxification ability is maintained at a high level for a long period. For example, porcine hepatocyte cultured using an insert (on day 21 of culture) have a metabolic ability of ammonia which can be improved by about 20 to 30-fold as compared with flat culture and by about 1.5 to 2.5-fold as compared with Matrigel, have a metabolic ability of lidocaine which can be improved by about 25 to 35-fold as compared with flat culture and by 25 about 1.5 to 2.5-fold as compared with Matrigel, and have a metabolic ability of diazepam which can be improved by about 20 to 30-fold as compared with flat culture and by about 1.3 to 2.0-fold as compared with Matrigel. Human hepatocytes cultured without insert (on day 5 of culture) have a metabolic ability of ammonia which can be improved by about 5 to 10-fold as compared with flat culture and by about 1.1 to 1.5-fold as compared with Matrigel. According to the above-described hepatocyte cultivation method, it is possible to form spheroid (spherical and having a diameter of 100 to 120 μm), which is difficult to achieve in flat culture.

The term "spheroid" means a three-dimensional spherical cell agglomerate. Formation and/or maintenance of spheroid indicate that physiological functions of the above-described spheroid are similar to those of living tissue, as compared with lone cell or irregular spheroid.

According to the hepatocyte high-dimensional cultivation method of the present invention, effects are obtained which are not obtained by conventional three-dimensional culture using a scaffold such as Matrigel. For example, mentioned as a morphological character is formation of a cell adhesion apparatus (also referred to as intercellular adhesion apparatus) and bile canaliculi between hepatocytes as features of high-dimensional culture, examined by a transmission electron microscope (see, FIGS. 2(c) and 2(d)).

The three-dimensional culture refers to a technique of sterically seed a cell into a scaffold and then, culturing the cell. A conventional method for culturing cells having adhesiveness is characterized in that cells are cultured on a plane of a vessel such as a petri dish (two-dimensional culture). In contrast, in the three-dimensional cultivation method, since cells are present sterically, an environment in organisms is simulated in a culture environment, tissue is allowed to form, and the tissue can be observed. As the three-dimensional cultivation method, for example, collagen sandwich culture or the like is mentioned (see, Chandra P, Lecluyse E L, Brouwer K L. Optimization of culture conditions for determining hepatobiliary disposition of taurocholate in sandwich-cultured rat hepatocyte. In Vitro Cell Dev Biol Anim. 2001 June; 37(6): 380-5.).

The high-dimensional culture refers to culture in which individual culture cells form "assembled" cell population while mutually collaborating and integrating. If a liver tissue and pancreas Langerhans islet (pancreatic islet) having high order functions can be formed by reconstruction in a growth system of cells which have been isolated and removed from liver and pancreas, an innovative new technology leading to regeneration treatments of hepatic diseases and diabetic mellitus can be established. It can also be a culture technique having a possibility of bringing an extremely large social benefit such as "industrial production of tissues and organs" which can be also referred to as a dream of mankind, in the future.

While the three-dimensional culture means steric (three-dimensional) culture of cells which have been cultured on plane, the high-dimensional culture is a further progressed cultivation method which is steric and in which activity as tissue is made possible. Functioning as tissue can be explained that single or several types of cell (in liver, hepatic cell, stellate cell) constitute tissue in a culture environment, and exhibit a function of the subject organ. In such high-dimensional culture, formation of a cell adhesion apparatus and bile canaliculi are promoted, and functions of cells are exhibited to their maximum.

Figure 2D:
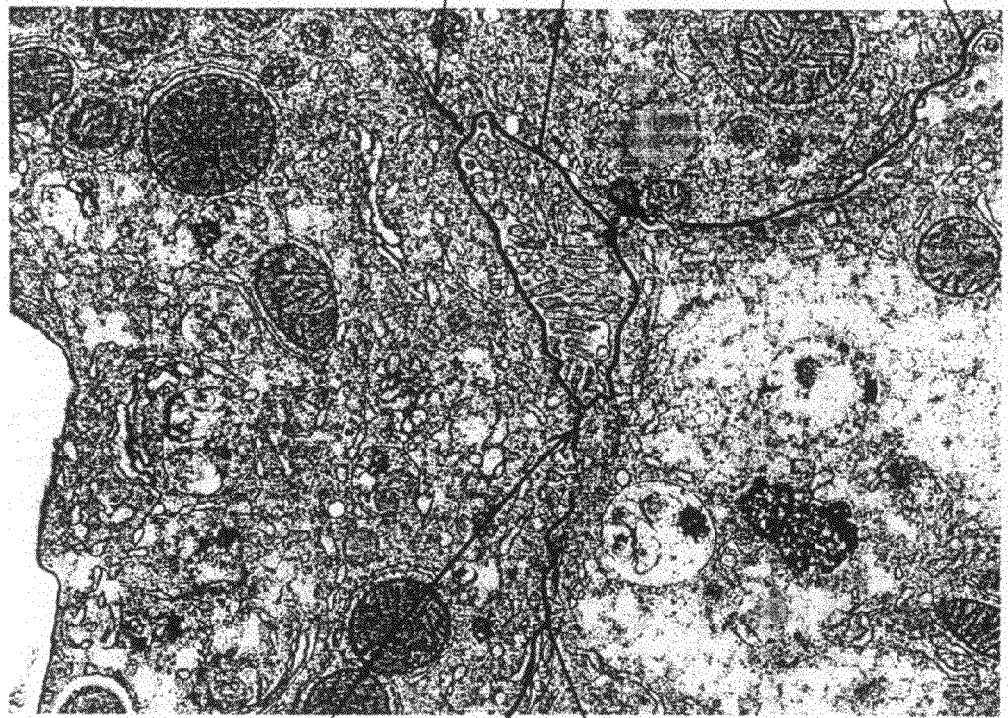
FIG. 2(d) is a drawing for explaining a cell adhesion apparatus and bile canaliculi in FIG. 2(c). Numerical reference 5 shows a cell adhesion apparatus, and numerical reference 6 shows a bile canaliculi. Numerical reference 7 shows an interface between cells.

A cell adhesion apparatus 5 means an apparatus formed as a result of recruitment of cell skeletons around a central adhesive molecule for cell adhesion by cells, and examples thereof include adherence junction, tight junction, desmosome and hemidesmosome (see, FIGS. 2(c) and 2(d)). In multicellular organisms, individual cells are not present independently but mutually adhere or adhere to extracellular matrices. Mutual cell bond, and bonding of cells to extracellular matrices are called as cell adhesion. The former is called cell adhesion (also referred to as cell-to-cell adhesion) and the latter is called cell-matrix adhesion, and in some cases, only the former is referred to as cell adhesion in a narrow sense. The basis of cell adhesion is that cells mutually or cells and matrices come into direct contact and achieve adhesion. However, in some cases cells have an apparatus for cell adhesion recruiting cell skeletons for adhesion. Cell adhesion occurs by an intermolecular interaction of cell adhesion molecules, and also an adhesion apparatus is formed around an adhesion molecule. Conditions of cell adhesion vary depending on the type of cells and tissue. In epithelium, it is common that epithelial cells are mutually strongly adhered, to form a specialized adhesion structure such as adherence junction, tight junction and desmosome, while, culture cells adhered to a basement membrane as an extracellular matrix and forming hemidesmosome have a cell adhesion apparatus, thereby an adhesion structure can be stabilized, the whole cell morphology can be maintained, and a tissue structure can be maintained. Such an adhesion structure also is enables to exhibit a function of preventing invasion of molecules, bacteria and viruses from outside by filling a gap between cells. Furthermore, with such adhesion, it becomes also possible to transmit a signal into a cell and express cell characteristics such as cell differentiation and growth.

A bile canaliculi 6 is a gap formed between two hepatocytes and is a tube having a diameter of about 0.5 to 1 μm (see, FIGS. 2(c) and 2(d)). Bile produced in a hepatic cell is secreted into a bile canaliculi. Formation of a bile canaliculi shows reconstruction of high-dimensional culture, that is, tissue analogous to liver.

According to the pancreatic islet high-dimensional cultivation method of the present invention, insulin, a production component originally contained in pancreatic islet, can be produced efficiently by culturing pancreatic islet derived from porcine or human. In the cultivation method of the present invention, the insulin production ability (high glucose culture) of the resultant pancreatic islet is preferably about 5 to 15-fold as compared with flat culture. It is preferable that the insulin production amount can be regulated by sensing the glucose concentration in culture medium, and it is preferable that the production amount is 0.4 to 0.8 μg/l (10 pancreatic islets), 0.7 to 1.5 μg/l (10 pancreatic islets) and 0.5 to 1.2 μg/l (10 pancreatic islets), respectively, in culture in low glucose concentration, high glucose concentration and then, low glucose concentration, and it is preferable that the difference in the insulin production amount between low glucose concentration and high glucose concentration being at least 0.3 μg/l (10 pancreatic islets). Insulin secretion to glucose stimulation in high glucose concentration is preferably at least 1.5-fold, more preferably at least 2.0-fold as compared with in low glucose concentration. Furthermore, it is preferable that the insulin production amount lowers when the glucose concentration is returned from high to low, and it is preferable that the difference in the insulin production amount is at least 0.3 μg/l (10 pancreatic islets). The above-described pancreatic islet cultivation method is preferable, since culture is possible together with successful maintenance of a shape of spheroid, that is difficult in flat culture.

As the inspection method of cultured pancreatic islets, a method is mentioned in which the following 4 items as morphological criteria are evaluated at 5 levels (1 to 5 points) (see, literature: Matsumoto S, Qualley S A, Goel S, et al., Effect of the two-layer (University of Wisconsin solution-Perfluorochemical plus 02) method of pancreas preservation on human islet isolation as assessed by Edmonton isolation protocol. Transplantation 2002; 74: 1414).

1. Shape

Evaluation is performed at 5 levels of "flat: 1 point", "approximately flat: 2 points", "irregularly spherical: 3 points", "approximately spherical: 4 points", and "spherical: 5 points".

Among them, "spherical: 5 points" is the most preferable.

2. Border Shape

Evaluation is performed at 5 levels of "irregular: 1 point", "approximately irregular: 2 points", "somewhat well-rounded: 3 points", "approximately well-rounded: 4 points", and "well-rounded: 5 points". Among these, "well-rounded: 5 points" is most preferable.

3. Integrity

Evaluation is performed at 5 levels of "fragmented: 1 point", "approximately fragmented: 2 points", "somewhat solid/compact: 3 points", "approximately solid/compact: 4 points", and "solid/compact: 5 points". Among these, "solid/compact: 5 points" is most preferable.

4. Diameter

Evaluation is performed at 5 levels of "smaller than 100 μm for individual cultured pancreatic islets (all <100 μm): 1 point", "100 to 150 μm for individual cultured pancreatic islets: 2 points", "125 to 175 μm for individual cultured pancreatic islets: 3 points", "150 to 200 μm for individual cultured pancreatic islets: 4 points", and "larger than 200 μm for at least 10% of individual cultured pancreatic islets (>10%>200 μm): 5 points". Among these, "larger than 200 μm for at least 10% of individual cultured pancreatic islets: 5 points" is most preferable.

For pancreatic islets obtained by the cultivation method of the present invention using a peptide hydrogel as a scaffold, it is preferable in the terms of morphology that the shape is at least 3 points, the border shape is at least 3 points, the integrity is at least 3 points, the diameter is at least 3 points, and the sum of the evaluation values is at least 12 points, it is more preferable that the shape is at least 4 points, the border shape is at least 4 points, the integrity is at least 4 points, the diameter is at least 4 points, and the sum of the evaluation values is at least 16 points, and it is most preferable that the shape is at least 5 points, the border shape is at least 5 points, the integrity is at least 5 points, the diameter is at least 5 points, and the sum of the evaluation values is 20 points. Regarding the function of pancreatic islets obtained by the cultivation method of the present invention, insulin secretion in response to glucose stimulation in high glucose is preferably at least 1.5-fold, more at least 2.0-fold as compared with in low glucose.

In the above-described criteria, the shape "flat" means that when a pancreatic islet is considered to be elliptic sphere, the ratio of major axis/minor axis is at least 10, the shape "approximately flat" means that the above-described ratio of major axis/minor axis is at least 5 and less than 10, the shape "irregularly spherical" means that the above-described ratio of major axis/minor axis is at least 2 and less than 5, the shape "approximately spherical" means that the above-described ratio of major axis/minor axis is at least 1.2 and less than 2, and the shape "spherical" means that the above-described ratio of major axis/minor axis is less than 1.2.

The "irregular" border shape means that at least 90% of the border of pancreatic islet are rough and lacking smoothness, the "approximately irregular" border shape means that at least 50% and less than 90% of the border of pancreatic islet are irregular, the "somewhat well-rounded" border shape means that at least 20% and less than 50% of the border of pancreatic islet are irregular, the "approximately well-rounded" border shape means that at least 10% and less than 20% of the border of pancreatic islet are irregular, and the "well-rounded" border shape means that less than 10% of the border of pancreatic islet are irregular.

The "fragmented" integrity means that at least 80% of all pancreatic islets have constriction, the "approximately fragmented" integrity means that 60 to 80% of all pancreatic islets have constriction, the "somewhat solid/compact" integrity means that 40 to 60% of all pancreatic islets have constriction, the "approximately solid/compact" integrity means that 20 to 40% of all pancreatic islets have constriction, and the "solid/compact" integrity means that at most 20% of all pancreatic islets have constriction.

The diameter "smaller than 100 μm for individual cultured pancreatic islets" means that diameters of individual cultured pancreatic islets are all smaller than 100 μm, the diameter "100 to 150 μm for individual cultured pancreatic islets" means that diameters of individual cultured pancreatic islets are in a range of 100 to 150 μm, the diameter "125 to 175 μm for individual cultured pancreatic islets" means that diameters of individual cultured pancreatic islets are in a range of 125 to 175 μm, the diameter "150 to 200 μm for individual cultured pancreatic islets" means that diameters of individual cultured pancreatic islets are in a range of 150 to 200 μm, and the diameter "larger than 200 μm for at least 10% of individual cultured pancreatic islets" means that at least 10% of individual cultured pancreatic islets are larger than 200 μm.

Insulin secretion in response to glucose stimulation (also referred to as glucose responsive insulin secretion) means that a pancreatic islet perceives, for example, a change from low glucose concentration to high glucose concentration (glucose stimulation) in culture medium and promotes insulin secretion. Insulin is an only hormone that acts toward lowering of blood glucose, and is secreted from .beta. cell in pancreas Langerhans islet (pancreatic islet) in response to blood glucose concentration. When the pancreatic islet function is excellent, insulin is secreted appropriately in response to variation in glucose concentration, while when the pancreatic islet function is poor, such responsiveness to glucose becomes poor. In cultured pancreatic islet, the ratio of the amount of insulin secreted in low glucose concentration to the amount of insulin secreted in high glucose concentration (the amount of insulin secreted in high glucose concentration/the amount of insulin secreted in low glucose concentration) (represented as stimulation index; SI) is comparatively investigated, for evaluating the pancreatic islet function (see, Berger H, Knoch K P, Meisterfeld R, Jager M, Ouwendijk J, Kersting S, Saeger H D, Solimena M., Effect of oxygenated perfluorocarbons on isolated rat pancreatic islets in culture. Cell Transplant. 2005; 14(7): 441-8), and the SI value is preferably at least 1.5, more preferably at least 2.0.

High glucose culture refers to a culture condition of a glucose concentration in culture medium of 360 g/l to 450 g/l, and low glucose culture refers to a culture condition of a glucose concentration in culture medium of 60 g/l to 100 g/l.

The cell culture obtained as described above can be suitably applied to regenerative medicine, cell preparation, useful substance production (bioreactor), investigation and research of function of tissue, organ and internal organ, screening of new drugs, animal experiment substitute methods for evaluating influences of endocrine disrupting chemicals, and cell chips, including cell transplantation, and bioartificial organs such as bioartificial liver and bioartificial pancreatic islet.

The term "cell culture" means a suspension prepared by suspending a cell cultured using a peptide hydrogel of the present invention as a scaffold, in a medium, isotonic solution or buffering solution, together with the above-described scaffold. The medium, isotonic solution or buffering solution is appropriately selected so as to fit the above-described cell.

In this description, the cell preparation includes the above-described cell cultures as they are, and cell agglomerates such as pellets condensed by filter filtration. Furthermore, the above-described cell preparation can also be freeze-preserved with a protective agent such as DMSO added to the preparation. The cell preparation can be subjected to treatments under conditions by which proteins of pathogenic cells denature while leaving the function as the cell preparation, such as a heat treatment, radiation treatment and mitomycin C treatment, for safer utilization thereof.

The administration form (transplantation method) of the above-described cell preparation using hepatocyte or pancreatic islet include, for example, a method in which small dissection is made at lower right abdomen, a narrow blood vessel of mesenterium is exposed and a catheter is inserted into this under direct vision and cells are transplanted, a method in which hepatic portal is identified by echo, a catheter is needled and cells are transplanted, and a method in which spleen is needled directly under abdominal echo guide and transplantation into spleen is performed (see, Nagata H, Ito M, Shirota C, Edge A, McCowan T C, Fox I J: Route of hepatocyte delivery affects hepatocyte engraftment in the spleen. Transplantation, 76(4): 732-4, 2003). Among these, the method of performing cell transplantation by echo is more preferable because of less invasion, and the method of performing transplantation into spleen by directly needling spleen under abdominal echo guide is most preferable. The administration amount (transplantation amount) of the cell preparation is preferably $1\times10^8$ to $1\times10^{10}$ cells/individual, further preferably $5\times10^8$ to $1\times10^{10}$ cells/individual, and most preferably $1\times10^8$ to $1\times10^{10}$ cells/individual. The administration amount (transplantation amount) can be appropriately altered depending on the age, body weight and symptoms of a patient to receive the therapy.

Hepatocyte and pancreatic islet obtained by the present invention can be used as sources for bioartificial liver and bioartificial pancreas targeting hepatic failures and diabetes mellitus, respectively.

The above-described bioartificial organs using hepatocyte or pancreatic islet include, for example, hybrid type artificial organs using bioreactors of diffusion chamber type, microcapsule type and hollow fiber type obtained by enclosing a cell cultured using a peptide hydrogel of the present invention as a scaffold, into a device made of a polymer material, together with the above-described scaffold. Bioartificial organs include three forms: one mounted outside the body and connected to a blood vessel, one indwelled in the body and connected to a blood vessel, and one not connected to a blood vessel and indwelled in abdominal cavity. Hepatocyte or pancreatic islet obtained by the method of the present invention can be used in any form of bioartificial organs.

As the bioreactor to be used as the bioartificial organ, commercially available reactors can be used. For example, various types such as Hepat Assist for bioartificial liver treatment using porcine hepatocytes developed mainly by Demetriou, et al. in Cedars-Sinai Medical center (Los Angeles, Calif., US) under an assist by Circe Biomedical Inc. (Lexington, Mass. US) (see, Hui T, Rozga J, Demetriou A A. J Hepatobiliary Pancreat Surg 2001; 8: 1-15.), and MELS (Modular Extracorporeal Liver System) by Gerlach, et al. in German using porcine hepatocytes are known. These reactors can be used, of course, in the present invention, however, since there is no foothold for adhesion of cells, there is a tendency that cell is only filled in spaces in hollow fibers or in spaces outside hollow fibers, giving a floating condition. In general, cell show a tendency that no sufficient differential function is exhibited under a floating condition and furthermore, collide with surrounding cells, and easily stimulated by stress.

Therefore, preferable in the present invention are bioreactors containing hollow fibers, nonwoven fabric and peptide hydrogel so that a foothold can be provided for hepatocyte.

As the hollow fiber membrane, any type of membranes can be used providing substance exchange is not disturbed by cell adhesion to the membrane surface. Specifically, commercially available membranes conventionally used for medical treatment, for example, polysulfone membranes, and ethylene-vinyl acetate random copolymer-saponified material membranes (for example, trade name: Evapol, available from Kuraray Medical Inc.) and the like are preferable. Commercially available hollow fiber membranes include dialysis membranes (pore size: to 5 nm), plasma component separation membranes (pore size: 20 to 30 nm) and plasma separation membranes (pore size: 30 to 200 nm), depending on its application.

As the nonwoven fabric, those processed and modified so that cell can adhere to the fabric are preferable. Among these, polytetrafluoroethylene (PTFE) processed with poly(amino acid) urethane (PAU) is preferable from the viewpoint of easiness of processing thereof. Furthermore, those processed with basement membrane are also preferable (see, Katsumi Mochida, et al., Construction of artificial tissue using basement membrane formation technology, Regeneration Medicine. Vol. 5, No. 3, p. 57-63, 2006).

Using one embodiment of the bioreactor of the present invention as an example, manufacturing processes thereof are shown in FIG. 13. Hollow fibers 12 are arranged on nonwoven fabric 11 equipped with lining 10 (see, FIG. 13 (a)). Here, a slit 13 is made on the nonwoven fabric 11 equipped with lining 10. This is wound in the form of roll (see, FIG. 13 (*b*)). FIG. 13 (*c*) is an X-X line cross-section. The resultant roll is incorporated in a cylindrical vessel 15 equipped with liquid leak prevention parts 14 on both ends, obtaining a bioreactor 16. The bioreactor 16 is equipped with a cell injection port 17 and a discharge port 18 by which a cell sample can be collected, and the slit 13 is disposed so as to communicate with the cell injection port 17. Furthermore, the bioreactor 16 is equipped with a liquid inlet 19 and a liquid outlet 20. The liquid inlet 19 and the liquid outlet 20 communicate with the inside of the hollow fiber 12. The liquid inlet 19 and the liquid outlet 20 constitute a blood inflow port and a blood outflow port, respectively, in a bioartificial organ.

The method of filling cell or cell culture in a bioreactor include, for example, a method of culturing cell in a test tube and filling a bioreactor with a necessary number of cells, and a method of processing the inside of a bioreactor previously with PuraMatrix of SEQ ID NO:1 and culturing cells therein. In both cases, it is preferable to inject a cell suspension through a cell injection port equipped on the reactor using a 10 to 50 ml injection syringe, for filling the cell.

Treatment with a bioartificial organ using such a bioreactor is preferably carried out by a device integrating functions of 1) real time monitoring of inflow pressure and outflow pressure of an artificial organ reactor, 2) actuation of alarm in generation of bubbles, and 3) warming (37° C.) of the reactor, for safe and scientific operation.

The bioreactor of the present invention can also be applied suitably for useful substance production, investigation and research of function of tissue, organ and internal organ, screening of new drugs, and animal experiment substitute methods for evaluating influences of endocrine disrupting chemicals. The bioreactor of the present invention can be used as a bioreactor having a protein production ability, gluconeogenesis ability, urea production ability, blood detoxification and purification ability, and metabolic abilities of amino acid, carbohydrate and lipid, as functions of hepatocyte. Regarding detoxification, for example, ammonia, diazepam and lidocaine can be metabolized. The metabolic rates for porcine hepatocyte are preferably 20 to 100%, 15 to 100%, and 20 to 100%, and more preferably 30 to 100%, 25 to 100%, and 25 to 100%, respectively. The ammonia metabolic rate of human hepatocyte is preferably 15 to 100%, more preferably 20 to 100%.

The bioartificial pancreatic islet of the present invention can be used, for example, for insulin production which is a function of pancreatic islet. It is preferable that the insulin production amount can be regulated by sensing the glucose concentration in culture medium, and the production amount is preferably 0.4 to 0.8 µg/l (10 pancreatic islets), 0.7 to 1.5 µg/l (10 pancreatic islets) and 0.5 to 1.2 µg/l (10 pancreatic islets), respectively, in culture in low glucose concentration, high glucose concentration and then, low glucose concentration, and it is preferable that the difference in the insulin production amount between low glucose concentration and high glucose concentration is at least 0.3 µg/l (10 pancreatic islets). Insulin secretion in response to glucose stimulation in high glucose concentration is preferably at least 1.5-fold, more preferably at least 2.0-fold compared with in low glucose concentration. Furthermore, it is preferable that the insulin production amount lowers when the glucose concentration is returned from high to low, and it is preferable that the difference in the insulin production amount is at least 0.3 µg/l (10 pancreatic islets).

The bioartificial liver of the present invention can be used, for example, for production of physiologically active substances such as serum albumin as a production component and various coagulation factors originally contained in hepatocyte. Production of serum albumin can be carried out by purifying the resultant culture medium by methods usually used for purification of protein such as affinity column.

The bioartificial pancreatic islet of the present invention can be used, for example, for production of insulin, a production component originally contained in pancreatic islet. Production of insulin can be carried out by purifying the resultant culture medium by methods usually used for purification of protein such as affinity column.

The bioartificial liver of the present invention can be used for animal experiment substitute methods in clinical experiments such as screening of new drugs. For example, one-third of causes for drop out of novel medicinal nominated compounds in clinical tests is that pharmacokinetics predicted in animals using rat and dog is not reproduced in human. The cause thereof is largely correlated with a difference in metabolism between species. Then, PhoenixBio Co., Ltd. started, in collaboration with Daiichi Pharmaceutical Co., Ltd., a business for the purpose of shortening study period and enhancing success probability of development of medical products, by predicting drug metabolism in human in ADME test (test of administering R1 labeled compound to animals and checking absorption, distribution, metabolism and excretion) using chimera mice having human hepatocyte. As is understood from their planning of sales of 130 million yen, bioartificial livers providing prediction of data in human are very useful in development of medical products. However, in this human hepatocyte chimera mouse, 80 to 90% of the liver is substituted by human hepatocyte and the metabolic activity of rodents is 10-fold of human activity and thus, even if substituted by 90%, the activity level of the mouse is about the same as human, namely, there is a demerit that it cannot be used for evaluation of a compound showing no difference in metabolism between species. Furthermore, since an immunodeficient SCID mouse is used as the human hepatocyte chimera mouse, there is also a problem of many cases of deaths of chimera mice even if the administration amount is lower than the toxic dosage for usual mice. Additionally, because of 1) necessity of transplantation of human hepatocytes to animals and 2) complicated procedure of breeding animals, the project suggested by us is preferable owing to superiority to chimera mice. It is also preferable from the viewpoint of animal protection.

The bioartificial pancreatic islet of the present invention can be transplanted, for example, to diabetic patients whose population is increasing every year not only in Japan but also internationally. It is not an exaggeration to say that prevention and conquering of human diabetic mellitus are great objectives of human beings in the 21st century. Therefore, many drug manufacturers are working on the development of diabetes drugs.

Recently, manufacturing of transgenic (Tg) animals has become easy, and Tg animals with diabetes having various unique properties have been generated. For these Tg animals, establishment, maintenance, proliferation and supply of strains are laborious works. Since establishment of model animals needs long period and enormous energy and tolerance, it cannot be worked on deliberately under current quick passage of time. Furthermore, proliferation and maintenance of strains need manpower and equipments, and in the case of model animals whose role has been completed, there is also a risk of loss. Because of a difference between human diabetes and diabetic model animals, there is a problem of many cases of drop out at the clinical test stage of developed medical products. The bioartificial pancreatic islet of the present invention is preferable since it can solve such issues.

EXAMPLES

The present invention will be explained by examples shown below, but the present invention is not limited to these examples.

Example 1

Isolation and Culture of Porcine Hepatocytes

Large white male pigs (body weight: 15 to 20 kg) were used. 1.5 ml of ketalar for intramuscular injection was injected to cause sedation and then, auricular vein was acquired and 5 mg/kg of isozol and 1 mg/kg of musculax were administered intravenously to obtain muscle relaxation. After endotracheal intubation, peritoneotomy was performed under general anesthesia with sevoflurene under controlled ventilation by an artificial respirator. A liver lateral region of the pig was surgically excised (about 80 g), perfusion was performed through excised cross-section portal vein and hepatic vein. First, the excised liver was perfused with a primary perfusion solution (sodium chloride 9 g/L, potassium chloride 0.42 g/L, sodium hydrogen carbonate 2.1 g/L, glucose 0.9 g/L, HEPES 4.78 g/L, ethylenediamine tetraacetic acid (EDTA) 0.37 g/L), subsequently, perfused with a secondary perfusion solution containing no EDTA (sodium chloride 9 g/L, potassium chloride 0.42 g/L, sodium hydrogen carbonate 2.1 g/L, glucose 0.9 g/L, HEPES 4.78 g/L). Thereafter, perfusion of the liver, kept at 39° C., was done with a dispase solution (sodium chloride 9 g/L, potassium chloride 0.42 g/L, sodium hydrogen carbonate 2.1 g/L, glucose 0.9 g/L, HEPES 4.78 g/L, dispase 8.4 g/L) (available from Godo Shusei K. K., Tokyo, Japan) and finally, with a collagenase solution (sodium chloride 9 g/L, potassium chloride 0.42 g/L, sodium hydrogen carbonate 2.1 g/L, glucose 0.9 g/L, HEPES 4.78 g/L, collagenase 0.5 g/L (available from Nitta Gelatin Inc., Osaka, Japan), calcium chloride monohydrate 0.55 g/L). After perfusion, a hepatic capsule was morcellated and hepatocytes were dispersed in the collagenase solution, and a cell suspension liquid was filtrated with 75 μm mesh, and this was centrifuged at a low speed (50 g, 2 minutes). The pellet was re-suspended in a primary washing liquid (sodium chloride 7 g/L, potassium chloride 0.46 g/L, calcium chloride monohydrate 0.13 g/L, HEPES 2.38 g/L, bovine serum albumin (BSA) 1.0 g/L (available from SIGMA), magnesium chloride hexahydrate 0.1 g/L, magnesium chloride heptahydrate 0.1 g/L, deoxyribonuclease (DNaseI) 0.1 g/L (available from Roche Mannheim Germany)), and furthermore, centrifuged at low speed (50 g, 75 seconds). This operation was repeated three times and then, the pellet was suspended in a secondary washing liquid (sodium chloride 7 g/L, potassium chloride 0.46 g/L, calcium chloride monohydrate 0.13 g/L, HEPES 2.38 g/L, bovine serum albumin 1.0 g/L (available from SIGMA), magnesium chloride hexahydrate 0.1 g/L, magnesium chloride heptahydrate 0.1 g/L). The isolated porcine hepatocytes were suspended in a hepatocyte culture medium (William's Medium E (available from SIGMA), 10% fetal bovine serum (available from SIGMA), insulin $1\times10^{-7}$ mol/L (GIBCOBRL13007-018) (available from GIBCO BRL), epithelial cell growth factor (EGF) 25 μg/L (available from SIGMA), dexametazone $1\times10^{-6}$ mol/L (available from SIGMA), penicillin $1\times10^{-5}$ U/L and streptomycin $1\times10^{-5}$ μg/L) and then, cultured with or without insert.

(Culture without Insert)

Cells were seeded ($2\times10^5$ cells/well) on 12-well plates coated with PuraMatrix of SEQ ID NO:1 (group A) and 12-well plates coated with collagen type I (monolayer) (group B) or Matrigel (group C) (BIOCOAT, available from Becton Dickinson Labware) and then, cultured for 18 hours at 37° C. under 5% $CO_2$ to obtain porcine hepatocytes which were used in the following Examples 2 to 6. Exchange of the medium was carried out every two days.

(Culture Using Insert)

An insert (available from Becton Dickinson BioScience) was used, and cell culture was carried out on a filter of the insert. In this method, the insert can be removed in exchanging the culture medium for new medium. As a result, mechanical damage on a scaffold due to medium exchange can be alleviated. PuraMatrix of SEQ ID NO:1 (group A), collagen type I (monolayer) (collagen is added on an insert, permeated in culture medium at room temperature overnight and then, cells are seeded) (group B), Matrigel (Matrigel is added on an insert, permeated in culture medium at room temperature overnight and then, cells are seeded) (group C), or collagen sandwich (hepatocytes are cultured, intervening between collagen monolayers: first, a collagen monolayer is placed and then, hepatocytes are seeded thereon, finally, a collagen monolayer is placed thereon, providing an environment similar to three-dimensional culture to cells) (group D), and cells were seeded ($2\times10^5$ cells/insert) and then, cultured for 18 hours at 37° C. under 5% $CO_2$ to obtain porcine hepatocytes which were used in the following Examples 2 to 6. Exchange of the medium was carried out every two days. In culture using PuraMatrix of SEQ ID NO:1 as a scaffold (group A), a method of sowing cells by the following processes was adopted.

1) PuraMatrix of SEQ ID NO:1 was diluted to 0.5% with phosphate buffered saline (PBS) at room temperature (RT).

2) Hepatocytes were suspended ($2\times10^5$ cells/ml) in PBS (RT), and then mixed with equal volume of the above-described PuraMatrix of SEQ ID NO:1 of 0.5% concentration in a 200 μl tube, where pipetting was performed in short while (within 5 seconds). Then, a mixture of hepatocytes suspended with PuraMatrix of SEQ ID NO:1+PBS was seeded at the bottom of the insert.

At this step, a hepatocyte culture medium was filled in advance, in a culture dish 12 well-plate into which an insert is to be placed, in order to avoid a damage of cells due to low pH of PuraMatrix of SEQ ID NO:1, as much as possible. Thereby, pH is adjusted to physiological pH.

3) An insert was placed for 5 minutes at RT and then, the insert was removed, and the hepatocyte culture medium in the culture dish 12-well plate was exchanged for new one quickly. Then, the inset was placed thereon.

4) PuraMatrix of SEQ ID NO:1 was left as it was at RT for 10 minutes to adjust its pH.

5) Furtheimore, the insert was removed at RT, and the hepatocyte culture medium in the culture dish 12-well plate was 10 exchanged for new one quickly. Then, the inset was placed thereon.

6) Operations 4) to (5) were carried out again and then, culture was performed in a culture vessel at 37° C. under 5% CO2 without any change.

Example 2

Morphological Study of Cultured Porcine Hepatocyte by Phase-Contrast Microscope and Electron Microscope (Culture without Insert)

Culture conditions of cultured porcine hepatocytes were observed on days 1, 7 and 14 of culture with a-phase-contrast microscope and compared between groups A and B. In the group using PuraMatrix of SEQ ID NO:1 (group A), cells kept a spherical morphology, and individual cells gradually formed an agglomerate (see, Photographs 1, 2 and 3 in FIG. 2 (a)). Culture conditions of porcine hepatocytes on day 5 of culture were observed with an electron microscope, as a result, formation of three-dimensional spheroid by hepatocytes was confirmed (FIG. 2 (b), Photograph 1: only PuraMatrix of SEQ ID NO:1, Photograph 2: porcine hepatocytes covering over PuraMatrix of SEQ ID NO:1, Photograph 3: porcine hepatocytes forming three-dimensional spheroid on PuraMatrix of SEQ ID NO:1, Photograph 4: porcine hepatocytes initiating to form three-dimensional spheroid on PuraMatrix of SEQ ID NO:1, Photograph 5: lower magnification image of Photograph 4, Photograph 6: porcine hepatocytes forming three-dimensional spheroid on PuraMatrix of SEQ ID NO:1). Recently, it has been known that when three-dimensional culture of cells is performed on scaffold, cell functions are improved and maintained. Since cultured porcine hepatocytes formed three-dimensional spheroid, it is strongly indicated that culturing porcine hepatocytes with PuraMatrix of SEQ ID NO:1 is useful for improvement of functions. In contrast, porcine hepatocytes cultured with collagen type I (monolayer) (group B) adhered in flat form to the surface of the culture flask (see, Photograph 4 in FIG. 2 (a)). The cell number decreased with time and formation of spheroid was not observed (see, Photographs 4, 5 and 6 in FIG. 2 (a)). As a result, it was clarified that it is more suitable for culture of porcine hepatocyte to use PuraMatrix of SEQ ID NO:1.

(Culture with Insert)

Culture conditions of cultured porcine hepatocytes were observed on day 3 of culture with a transmission electron microscope (see, FIGS. 2(c) and (d)). In the group using PuraMatrix of SEQ ID NO:1 (group A), a cell adhesion apparatus 5 and a bile canaliculi 6 were formed between hepatocytes, with a transmission electron microscope. This shows that the cell cultivation is done higher-dimensionally. In contrast, since formation of them was not seen in porcine hepatocytes cultured in the groups B, C and D. As a result, it was clarified that it is more suitable for culture of porcine hepatocyte to use PuraMatrix of SEQ ID NO:1 and an insert.

Example 3

Measurement of Viability of Porcine Hepatocyte (Culture without Insert)

In a survival test (live/dead test) (kit name: Live/Dead Double Staining Kit, catalogue No. QIA76, available from Cosmo Bio Co., Ltd. (Koto ward, Tokyo), the viability of porcine hepatocytes on days 1, 7 and 14 of culture was measured and compared for groups A and B. The live cells are entirely stained green, and the dead cells are entirely stained red. In the group using PuraMatrix of SEQ ID NO:1 (group A), most cells exhibited a green color, namely, survival of them was evident (see, Photographs 1, 2 and 3 in FIG. 3). In contrast, porcine hepatocytes cultured with collagen type I (monolayer) (group B) exhibited a green color on day 1 of culture, thereby indicating survival (see, Photograph 4 in FIG. 3). However, on days 7 and 14 of culture, only cells exhibiting a red color, indicating dead cell, were present (see, Photographs 5 and 6 in FIG. 3). Therefore, it was clarified that it is more suitable for culture of porcine hepatocyte to use PuraMatrix of SEQ ID NO:1 Since the appended Photographs are converted into white and black two tones, dyed colors are not expressed.

Example 4

Measurement of Metabolic Ability of Ammonia (Culture without Insert)

Figure 4A:
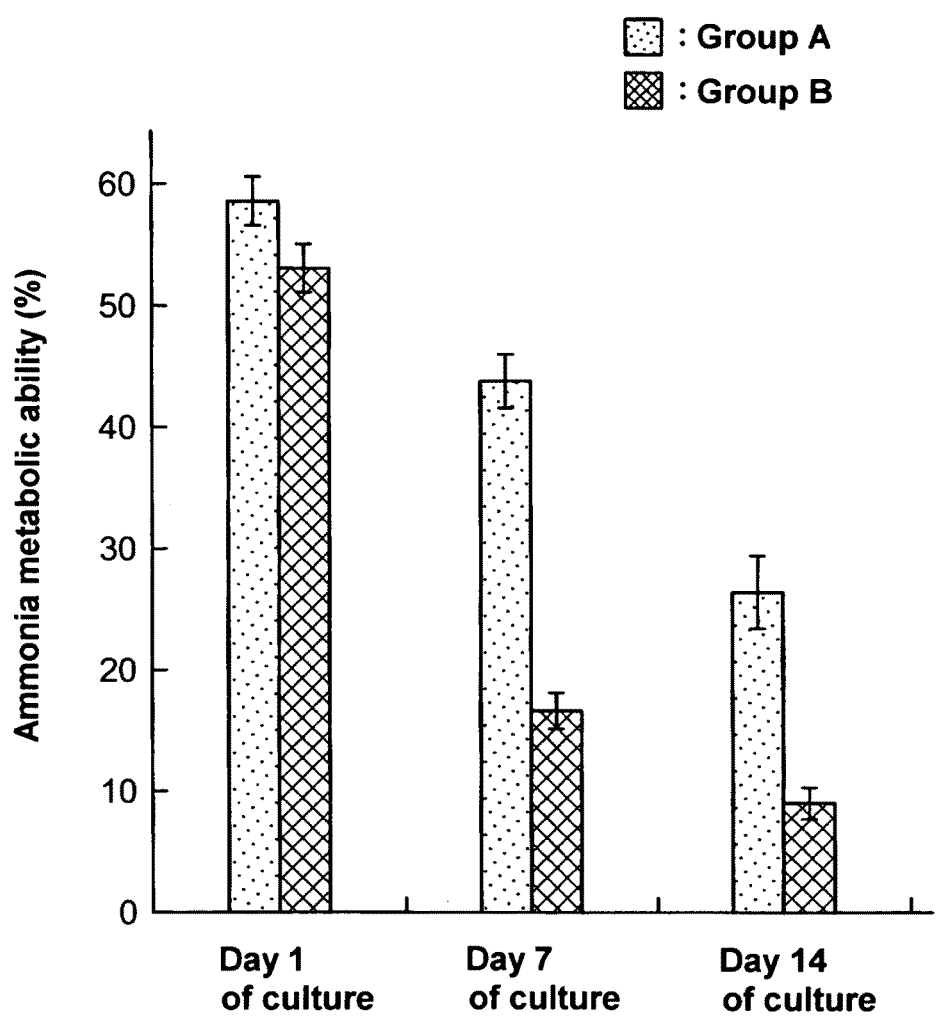
FIG. 4(a) is a graph comparing metabolic abilities of ammonia of porcine hepatocyte cultured by a cultivation method of the present invention using a peptide hydrogel as a scaffold (group A) and porcine hepatocyte cultured by a conventional cultivation method using collagen as a scaffold (group B).
Figure 4C:
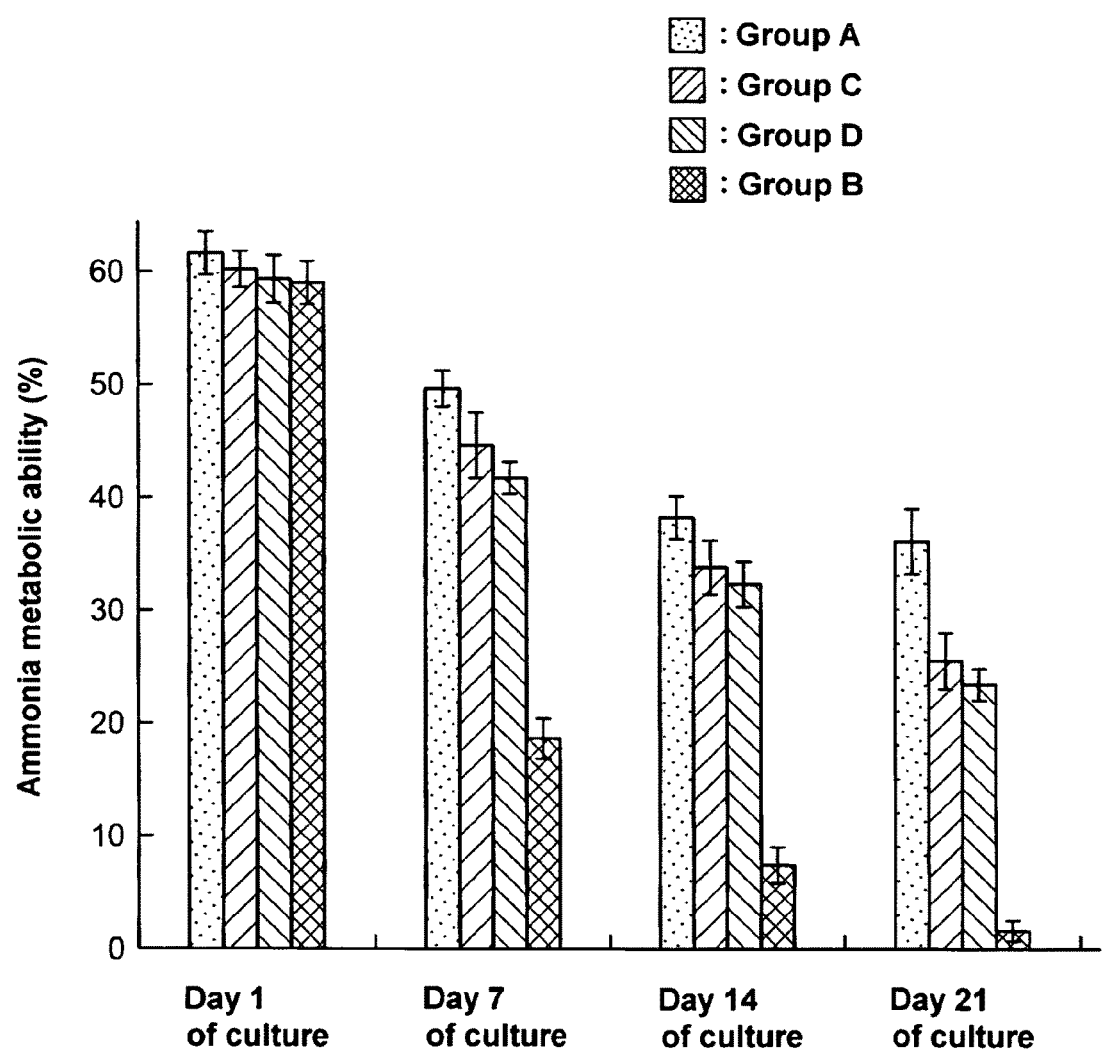
FIG. 4(c) is a graph comparing metabolic abilities of ammonia of porcine hepatocyte cultured using an insert, in a cultivation method of the present invention using a peptide hydrogel as a scaffold (group A), a conventional cultivation method using collagen as a scaffold (group B), a cultivation method using Matrigel as a scaffold (group C) and a cultivation method using collagen sandwich as a scaffold (group D), respectively.

The metabolic abilities of ammonia in cultured porcine hepatocyte were measured and compared between groups A and B. Ammonium sulfate (0.56 mM) was added to porcine hepatocyte media on days 1, 7 and 14 of culture, and the concentration of ammonia in the media after 24 hours was measured (FUJI DRI-CHEM SLIDE (Fuji Co., Tokyo, Japan)), and the metabolic rate was calculated. The results are shown in FIG. 4 (a) and Table 1(a). In the group using PuraMatrix of SEQ ID NO:1 (group A), the ammonia metabolic rate was significantly better as compared with collagen type I (monolayer) (group B). The expression "culture medium only" in the graph and table means that culture medium only, containing no cells, is measured, and the significant difference was tested, using ANNOVA.

TABLE 1(a)

|  | Group A | Standard deviation | Group B | Standard deviation | Culture medium only | Standard deviation |
|---|---|---|---|---|---|---|
| Day 1 of culture | 58.6 | 2.0 | 53.1 | 2.0 | 0.0 | 0.0 |
| Day 7 of culture | 43.8 | 2.2 | 16.6 | 1.5 | 0.0 | 0.0 |
| Day 14 of culture | 26.4 | 3.0 | 9.0 | 1.3 | 0.0 | 0.0 |

(Culture without Insert)

The metabolic abilities of ammonia in cultured porcine hepatocyte were measured and compared between groups A, B and C.

Ammonium sulfate (0.56 mM) was added to porcine hepatocyte media on days 1, 7 and 14 of culture, and the concentration of ammonia in the media after 24 hours was measured (FUJI DRI-CHEM SLIDE), and the metabolic rate was calculated. The results are shown in FIG. 4(b) and Table 1(b). In the group using PuraMatrix of SEQ ID NO:1 (group A), the ammonia metabolic rate was significantly better as compared with collagen type I (monolayer) (group B) and Matrigel (group C). The expression "culture medium only" in the graph and table means that culture medium only, containing no cells, is measured, and the significant difference was tested, using ANNOVA.

TABLE 1b

|  | Group A | Standard deviation | Group C | Standard deviation | Group B | Standard deviation | Culture medium only | Standard deviation |
|---|---|---|---|---|---|---|---|---|
| Day 1 of culture | 59.8 | 1.9 | 57.5 | 2.5 | 56.7 | 2.7 | 0.0 | 0.0 |
| Day 7 of culture | 44.3 | 2.4 | 39.9 | 2.9 | 17.2 | 1.8 | 0.0 | 0.0 |
| Day 14 of culture | 33.3 | 2.4 | 22.7 | 2.7 | 8.7 | 2.4 | 0.0 | 0.0 |

(Culture with Insert)

The metabolic abilities of ammonia in cultured porcine hepatocyte were measured and compared between groups A, B, C and D. Ammonium sulfate (0.56 mM) was added to porcine hepatocyte media on days 1, 7, 14 and 21 of culture, and the concentration of ammonia in the media after 24 hours was measured (FUJI DRI-CHEM SLIDE), and the metabolic rate was calculated. The results are shown in FIG. 4(*c*) and Table 1(c). In the group using PuraMatrix of SEQ ID NO:1 (group A), the ammonia metabolic rate was significantly better as compared with collagen type I (monolayer) (group B), Matrigel (group C) and collagen sandwich (group D). The expression "culture medium only" in the graph and table means that culture medium only, containing no cells, is measured, and the significant difference was tested, using ANNOVA.

TABLE 1(c)

|  | Group A | Group C | Group D | Group B | Culture medium only |
|---|---|---|---|---|---|
| Day 1 of culture | 61.6 | 60.2 | 59.3 | 59.0 | 0.0 |
| Day 7 of culture | 49.6 | 44.6 | 41.7 | 18.6 | 0.0 |
| Day 14 of culture | 38.2 | 33.8 | 32.3 | 7.4 | 0.0 |
| Day 21 of culture | 36.1 | 25.5 | 23.4 | 1.6 | 0.0 |
|  | Standard deviation | Standard deviation | Standard deviation | Standard deviation | Standard deviation |
| Day 1 of culture | 1.9 | 1.6 | 2.1 | 1.9 | 0.0 |
| Day 7 of culture | 1.6 | 2.9 | 1.4 | 1.8 | 0.0 |
| Day 14 of culture | 1.9 | 2.4 | 2.0 | 1.6 | 0.0 |
| Day 21 of culture | 2.9 | 2.5 | 1.4 | 0.9 | 0.0 |

Example 5

Measurement of Metabolic Ability of Lidocaine (Culture without Insert)

Figure 5A:
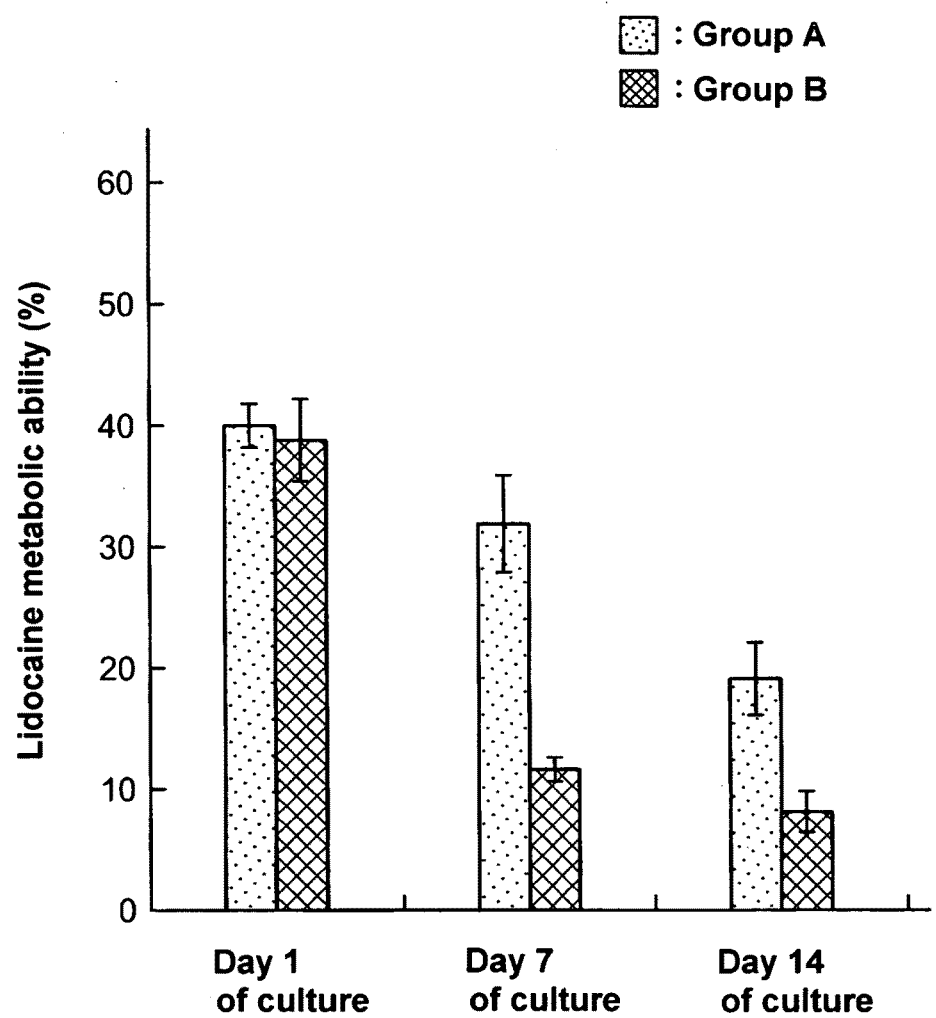
FIG. 5(a) is a graph comparing metabolic abilities of lidocaine in porcine hepatocyte cultured by a cultivation method of the present invention using a peptide hydrogel as a scaffold (group A) and porcine hepatocyte cultured by a conventional cultivation method using collagen as a scaffold (group B).
Figure 5C:
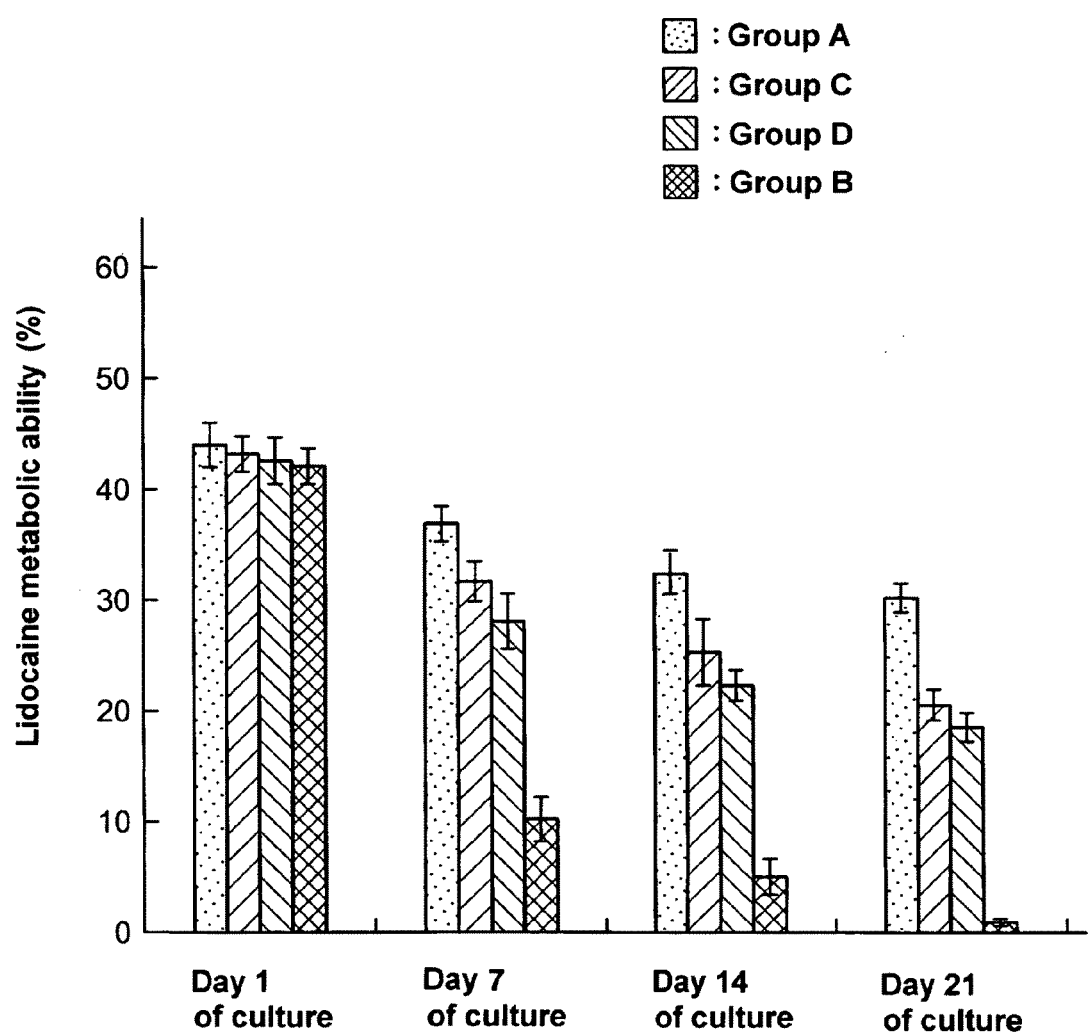
FIG. 5(c) is a graph comparing metabolic abilities of lidocaine in porcine hepatocyte cultured using an insert in addition, in a cultivation method of the present invention using a peptide hydrogel as a scaffold (group A), a conventional cultivation method using collagen as a scaffold (group B), a cultivation method using Matrigel as a scaffold (group C) and a cultivation method using collagen sandwich as a scaffold (group D), respectively.

The metabolic abilities of lidocaine in cultured porcine hepatocyte were measured and compared between groups A and B. Lidocaine (1 mg/ml) was added to porcine hepatocyte media on days 1, 7 and 14 of culture, and the concentration of lidocaine in the media after 10 24 hours was measured (entrusted to SRL K. K.), and the metabolic rate was calculated. The results are shown in FIG. 5 and Table 2. In the group using PuraMatrix of SEQ ID NO:1 (group A), the lidocaine metabolic rate was significantly better as compared with collagen type I (monolayer) (group B). The expression "culture medium only" in the graph and table means that culture medium only, containing no cells, is measured, and the significant difference was tested, using ANNOVA.

TABLE 2(a)

|  | Group A | Standard deviation | Group B | Standard deviation | Culture medium only | Standard deviation |
|---|---|---|---|---|---|---|
| Day 1 of culture | 40.0 | 1.8 | 38.8 | 3.4 | 0.0 | 0.0 |
| Day 7 of culture | 31.9 | 4.0 | 11.6 | 1.0 | 0.0 | 0.0 |
| Day 14 of culture | 19.1 | 3.0 | 8.1 | 1.7 | 0.0 | 0.0 |

(Culture without Insert)

The metabolic abilities of lidocaine in cultured porcine hepatocyte were measured and compared between groups A, B and C. Lidocaine (1 mg/ml) was added to porcine hepatocyte media on days 1, 7 and 14 of culture, and the concentration of lidocaine in the media after 24 hours was measured (entrusted to SRL K. K.), and the metabolic rate was calculated. The results are shown in FIG. 5(b) and Table 2(b). In the group using PuraMatrix of SEQ ID NO:1 (group A), the lidocaine metabolic rate was significantly better as compared with collagen type I (monolayer) (group B) and Matrigel (group C). The expression "culture medium only" in the graph and table means that culture medium only, containing no cells, is measured, and the significant difference was tested, using ANNOVA.

TABLE 2b

| | Group A | Standard deviation | Group C | Standard deviation | Group B | Standard deviation | Culture medium only | Standard deviation |
|---|---|---|---|---|---|---|---|---|
| Day 1 of culture | 40.8 | 2.1 | 39.1 | 2.2 | 38.4 | 2.4 | 0.0 | 0.0 |
| Day 7 of culture | 32.2 | 3.3 | 27.9 | 2.6 | 9.7 | 2.9 | 0.0 | 0.0 |
| Day 14 of culture | 21.0 | 1.5 | 15.5 | 2.5 | 6.1 | 2.8 | 0.0 | 0.0 |

(Culture with Insert)

The metabolic abilities of lidocaine in cultured porcine hepatocyte were measured and compared between groups A, B, C and D. Lidocaine (1 mg/ml) was added to porcine hepatocyte media on days 1, 7, 14 and 21 of culture, and the concentration of lidocaine in the media after 24 hours was measured (entrusted to SRL K. K.), and the metabolic rate was calculated. The results are shown in FIG. 5(b) and Table 2(b). In the group using PuraMatrix of SEQ ID NO:1 (group A), the lidocaine metabolic rate was significantly better as compared with collagen type I (monolayer) (group B), Matrigel (group C) and collagen sandwich (group D). The expression "culture medium only" in the graph and table means that culture medium only, containing no cells, is measured, and the significant difference was tested, using ANNOVA.

TABLE 2(c)

| | Group A | Group C | Group D | Group B | Culture medium only |
|---|---|---|---|---|---|
| Day 1 of culture | 44.0 | 43.2 | 42.6 | 42.1 | 0.0 |
| Day 7 of culture | 36.9 | 31.7 | 28.1 | 10.2 | 0.0 |
| Day 14 of culture | 32.4 | 25.3 | 22.3 | 5.0 | 0.0 |
| Day 21 of culture | 30.2 | 20.5 | 18.5 | 0.9 | 0.0 |
| | Standard deviation | Standard deviation | Standard deviation | Standard deviation | Standard deviation |
| Day 1 of culture | 2.0 | 1.6 | 2.1 | 1.6 | 0.0 |
| Day 7 of culture | 1.6 | 1.8 | 2.5 | 2.0 | 0.0 |
| Day 14 of culture | 1.8 | 3.0 | 1.4 | 1.6 | 0.0 |
| Day 21 of culture | 1.3 | 1.4 | 1.3 | 0.3 | 0.0 |

Example 6

Measurement of Metabolic Ability of Diazepam (Culture without Insert)

Figure 6A:
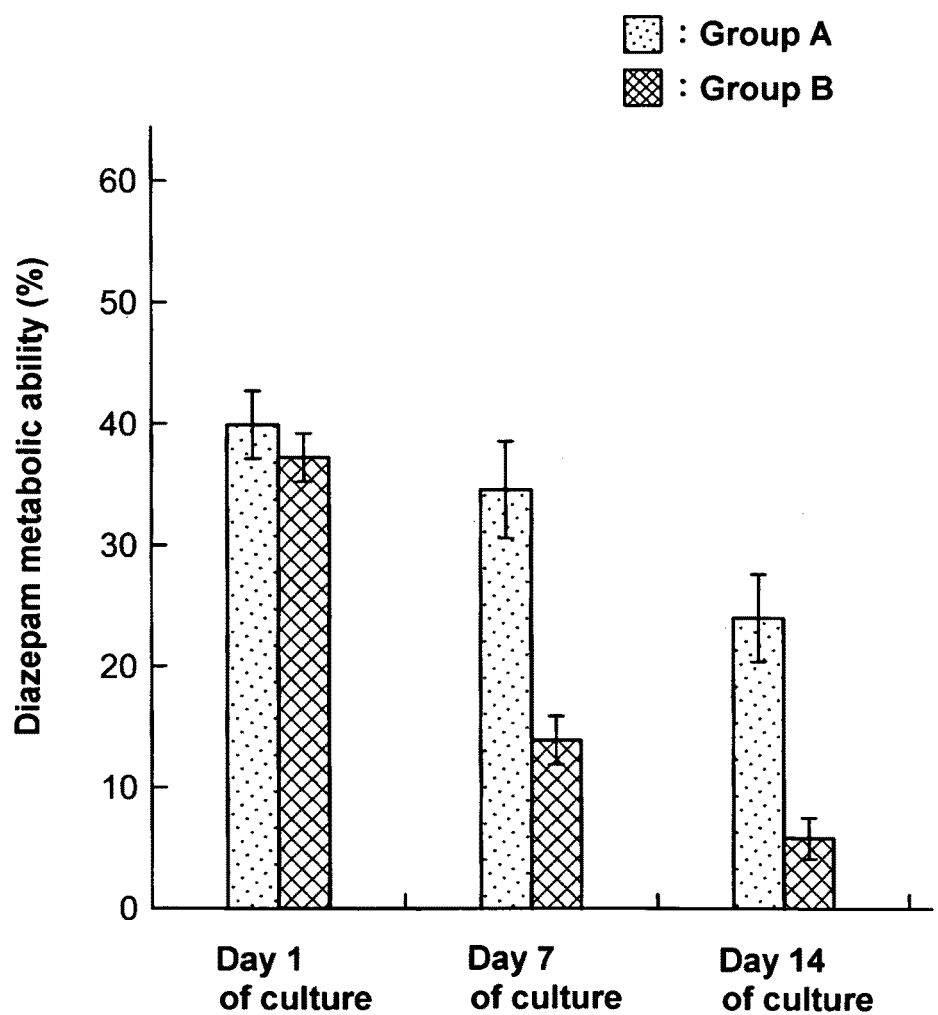
FIG. 6(a) is a graph comparing metabolic abilities of diazepam in porcine hepatocyte cultured by a cultivation method of the present invention using a peptide hydrogel as a scaffold (group A) and porcine hepatocyte cultured by a conventional cultivation method using collagen as a scaffold (group B).

The metabolic abilities of diazepam in cultured porcine hepatocyte were measured and compared between groups A and B. Diazepam (1 pg/ml) was added to porcine hepatocyte media on days 1, 7 and 14 of culture, and the concentration of diazepam in the media after 24 hours was measured (entrusted to SRL K. K.), and the metabolic rate was calculated. The results are shown in FIG. 6(a) and Table 3(a). In the group using PuraMatrix of SEQ ID NO:1 (group A), the diazepam metabolic rate was significantly better as compared with collagen type I (monolayer) (group B). The expression "culture medium only" in the graph and table means that culture medium only, containing no cells, is measured, and the significant difference was tested, using ANNOVA.

TABLE 3(a)

| | Group A | Standard deviation | Group B | Standard deviation | Culture medium only | Standard deviation |
|---|---|---|---|---|---|---|
| Day 1 of culture | 39.9 | 2.8 | 37.2 | 2.0 | 0.0 | 0.0 |
| Day 7 of culture | 34.6 | 4.0 | 13.9 | 2.0 | 0.0 | 0.0 |
| Day 14 of culture | 24.0 | 3.6 | 5.8 | 1.7 | 0.0 | 0.0 |

(Culture without Insert)

Figure 6B:
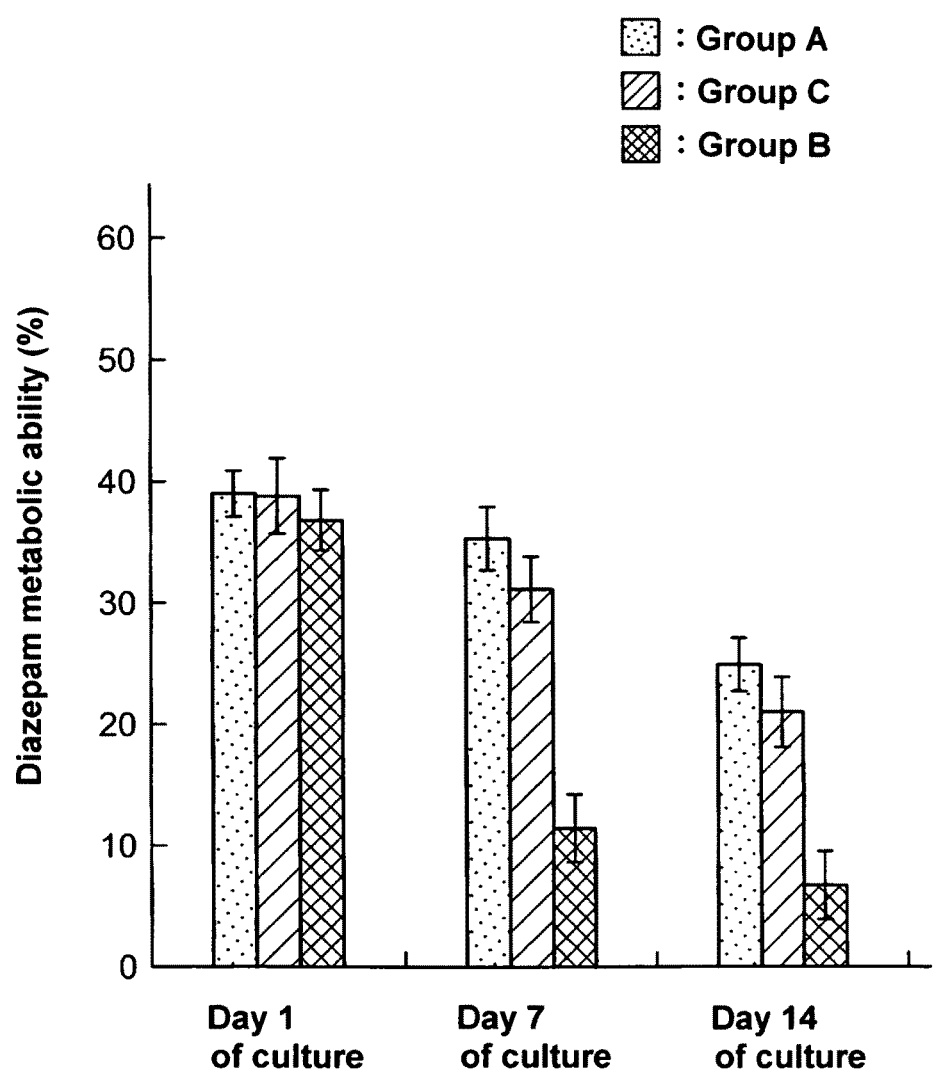
FIG. 6(b) is a graph comparing metabolic abilities of diazepam in porcine hepatocyte cultured by a cultivation method of the present invention using a peptide hydrogel as a scaffold (group A), porcine hepatocyte cultured by a conventional cultivation method using collagen as a scaffold (group B) and porcine hepatocyte cultured by a cultivation method using Matrigel as a scaffold (group C).

The metabolic abilities of diazepam in cultured porcine hepatocyte were measured and compared between groups A, B and C. Diazepam (1 pg/ml) was added to porcine hepatocyte media on days 1, 7 and 14 of culture, and the concentration of diazepam in the media after 24 hours was measured (entrusted to SRL K. K.), and the metabolic rate was calculated. The results are shown in FIG. 6(b) and Table 3(b). In the group using PuraMatrix of SEQ ID NO:1 (group A), the diazepam metabolic rate was significantly better as compared with collagen type I (monolayer) (group B) and Matrigel (group C). The expression "culture medium only" in the graph and table means that culture medium only, containing no cells, is measured, and the significant difference was tested, using ANNOVA.

TABLE 3b

|  | Group A | Standard deviation | Group C | Standard deviation | Group B | Standard deviation | Culture medium only | Standard deviation |
|---|---|---|---|---|---|---|---|---|
| Day 1 of culture | 39.0 | 1.9 | 38.8 | 3.1 | 36.8 | 2.5 | 0.0 | 0.0 |
| Day 7 of culture | 35.3 | 2.6 | 31.1 | 2.7 | 11.4 | 2.8 | 0.0 | 0.0 |
| Day 14 of culture | 24.9 | 2.2 | 21.0 | 2.9 | 6.7 | 2.8 | 0.0 | 0.0 |

(Culture with Insert)

Figure 6C:
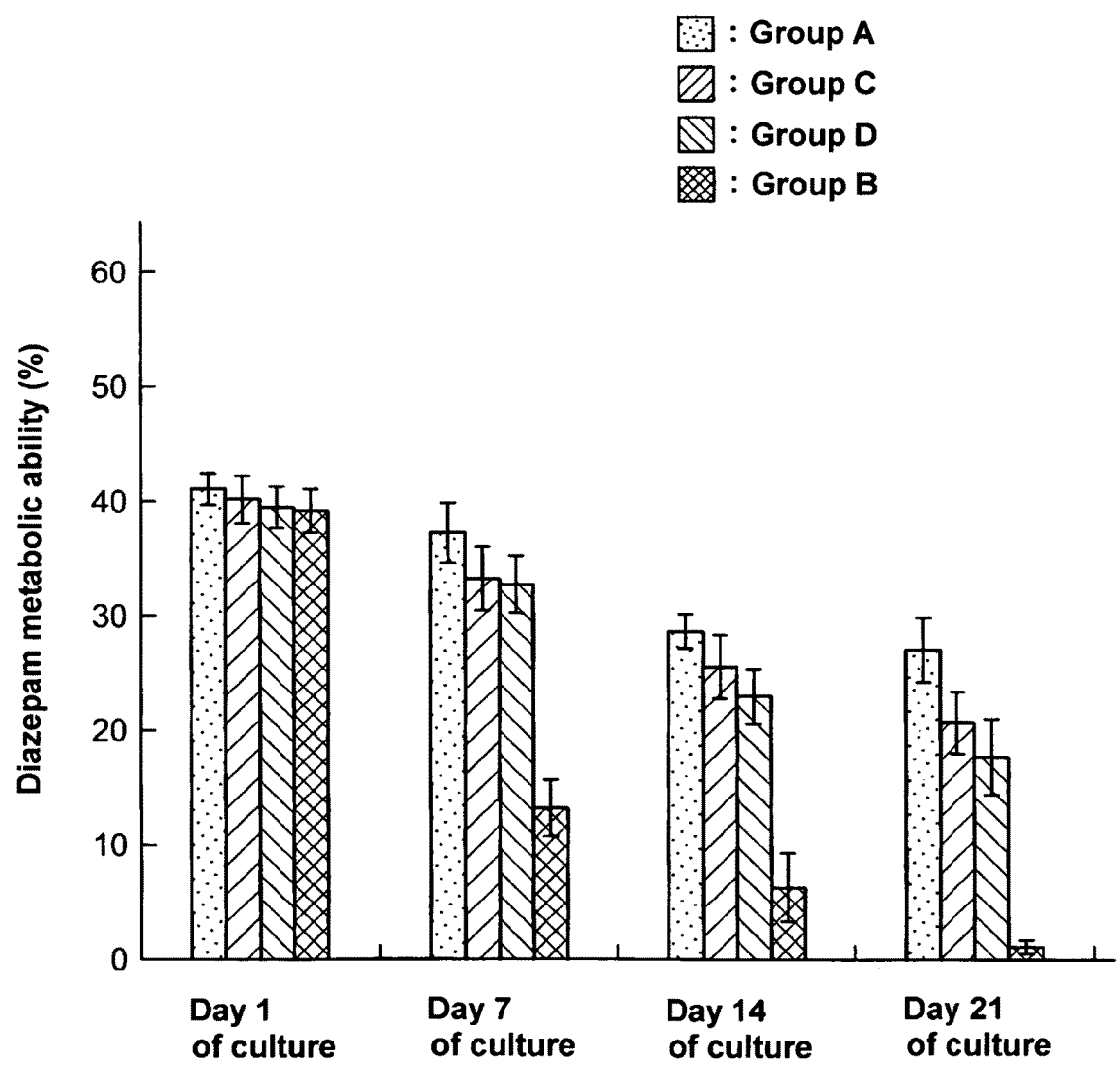
FIG. 6(c) is a graph comparing metabolic abilities of diazepam in porcine hepatocyte cultured by a cultivation method of the present invention using a peptide hydrogel as a scaffold (group A), a conventional cultivation method using collagen as a scaffold (group B), a cultivation method using Matrigel as a scaffold (group C) and a cultivation method using collagen sandwich as a scaffold (group D), as well as each cultivation methods with insert, respectively.

The metabolic abilities of diazepam in cultured porcine hepatocyte were measured and compared between groups A, B, C and D. Diazepam (1 pg/ml) was added to porcine hepatocyte media on days 1, 7, 14 and 21 of culture, and the concentration of diazepam in the media after 24 hours was measured (entrusted to SRL K. K.), and the metabolic rate was calculated. The results are shown in FIG. 6(c) and Table 3(c). In the group using PuraMatrix of SEQ ID NO:1 (group A), the diazepam metabolic rate was significantly better as compared with collagen type I (monolayer) (group B), Matrigel (group C) and collagen sandwich (group D). The expression "culture medium only" in the graph and table means that culture medium only, containing no cells, is measured, and the significant difference was tested, using ANNOVA.

TABLE 3(c)

|  | Group A | Group C | Group D | Group B | Culture medium only |
|---|---|---|---|---|---|
| Day 1 of culture | 41.1 | 40.2 | 39.5 | 39.2 | 0.0 |
| Day 7 of culture | 37.3 | 33.3 | 32.8 | 13.2 | 0.0 |
| Day 14 of culture | 28.7 | 25.6 | 23.0 | 6.3 | 0.0 |
| Day 21 of culture | 27.1 | 20.7 | 17.7 | 1.1 | 0.0 |
|  | Standard deviation | Standard deviation | Standard deviation | Standard deviation | Standard deviation |
| Day 1 of culture | 1.4 | 2.1 | 1.8 | 1.9 | 0.0 |
| Day 7 of culture | 2.6 | 2.8 | 2.5 | 2.5 | 0.0 |
| Day 14 of culture | 1.5 | 2.8 | 2.4 | 3.0 | 0.0 |
| Day 21 of culture | 2.8 | 2.7 | 3.3 | 0.6 | 0.0 |

Example 7

Isolation and Culture of Human Hepatocyte

Donor liver judged to be unsuitable for transplantation in the United States was obtained from National Disease Research Interchange via HUMAN & ANIMAL BRIDGING RESEARCH ORGANIZATION laboratory (Ichikawa city, Chiba prefecture, responsible person: Mr. Satoshi Suzuki) in the form of liver block (130 g) which was then separated into hepatocyte in the same manner as for the above-described isolation of porcine hepatocyte in Example 1. The isolated hepatocytes were seeded ($5\times10^5$ cells/well) on 6-well plates (without insert) coated with PuraMatrix of SEQ ID NO:1 (group A) or collagen type I (monolayer) (group B) and then, cultured for 18 hours at 37° C. under 5% $CO_2$ to obtain human hepatocytes which were used in the following Examples 8 and 9. Exchange of the medium was carried out every two days.

Example 8

Morphological Study of Cultured Human Hepatocyte by Phase-Contrast Microscope and Electron Microscope Culture conditions of cultured human hepatocytes were observed on days 1 and 5 of culture with a phase-contrast microscope and compared between groups A and B. In the group using PuraMatrix of SEQ ID NO:1 (group A), cells kept a spherical morphology, and individual cells gradually formed an agglomerate (see, Photographs 3 and 4 in FIG. 7(a)). Culture conditions of human hepatocytes on day 5 of culture were observed with an electron microscope, as a result, formation of three-dimensional spheroid by hepatocytes was confirmed (FIG. 7(b), Photograph 1: human hepatocytes covering over PuraMatrix of SEQ ID NO:1, Photograph 2: human hepatocytes initiating to form three-dimensional spheroid on PuraMatrix of SEQ ID NO:1, Photograph 3: magnification image of Photograph 1, Photograph 4: human hepatocytes forming three-dimensional spheroid on PuraMatrix of SEQ ID NO:1). Recently, it has been known that when three-dimensional culture of cells is performed on scaffold, cell functions are improved and maintained. Since cultured human hepatocytes formed three-dimensional spheroid, it is strongly indicated that culturing human hepatocytes with PuraMatrix of SEQ ID NO:1 is useful for improvement of functions. In contrast, human hepatocytes cultured with collagen type I (monolayer) (group B) adhered in flat form to the surface of the culture flask (see, Photograph 1 in FIG. 7(a)). The cell number decreased with time and formation of spheroid was not observed (see, Photographs 1 and 2 in FIG. 7(a)). As a result, it was clarified that it is more suitable for culture of human hepatocyte to use PuraMatrix of SEQ ID NO:1.

Example 9

Measurement of Metabolic Ability of Ammonia

Figure 8A:
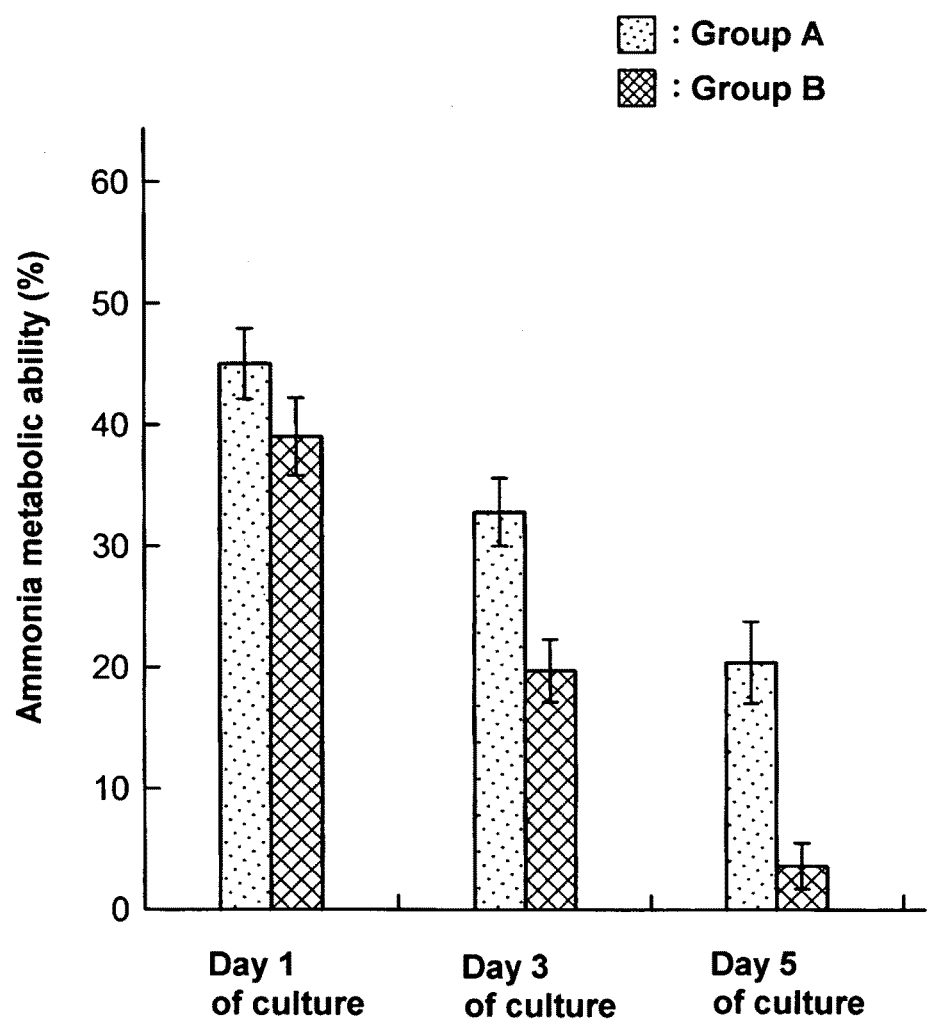
FIG. 8(a) is a graph comparing metabolic abilities of ammonia in human hepatocyte cultured by a cultivation method of the present invention using a peptide hydrogel as a scaffold (group A) and human hepatocyte cultured by a conventional cultivation method using collagen as a scaffold (group B).

The metabolic abilities of ammonia in cultured human hepatocytes were measured and compared between groups A and B. Ammonium sulfate (0.56 mM) was added to human hepatocyte media on days 1, 3 and 5 of culture without insert, and the concentration of ammonia in the media after 24 hours was measured (FUJI DRI-CHEM SLIDE), and the metabolic rate was calculated. The results are shown in FIG. 8(a) and Table 4(a). In the group using PuraMatrix of SEQ ID NO:1 (group A), the ammonia metabolic rate was significantly better as compared with collagen type I (monolayer) (group B). The expression "culture medium only" in the graph and table means that culture medium only, containing no cells, is measured, and the significant difference was tested, using ANNOVA.

TABLE 4(a)

|  | Group A | Standard deviation | Group B | Standard deviation | Culture medium only | Standard deviation |
|---|---|---|---|---|---|---|
| Day 1 of culture | 45.0 | 2.9 | 39.0 | 3.2 | 0.0 | 0.0 |
| Day 3 of culture | 32.8 | 2.8 | 19.7 | 2.6 | 0.0 | 0.0 |
| Day 5 of culture | 20.4 | 3.4 | 3.6 | 1.9 | 0.0 | 0.0 |

Figure 8B:
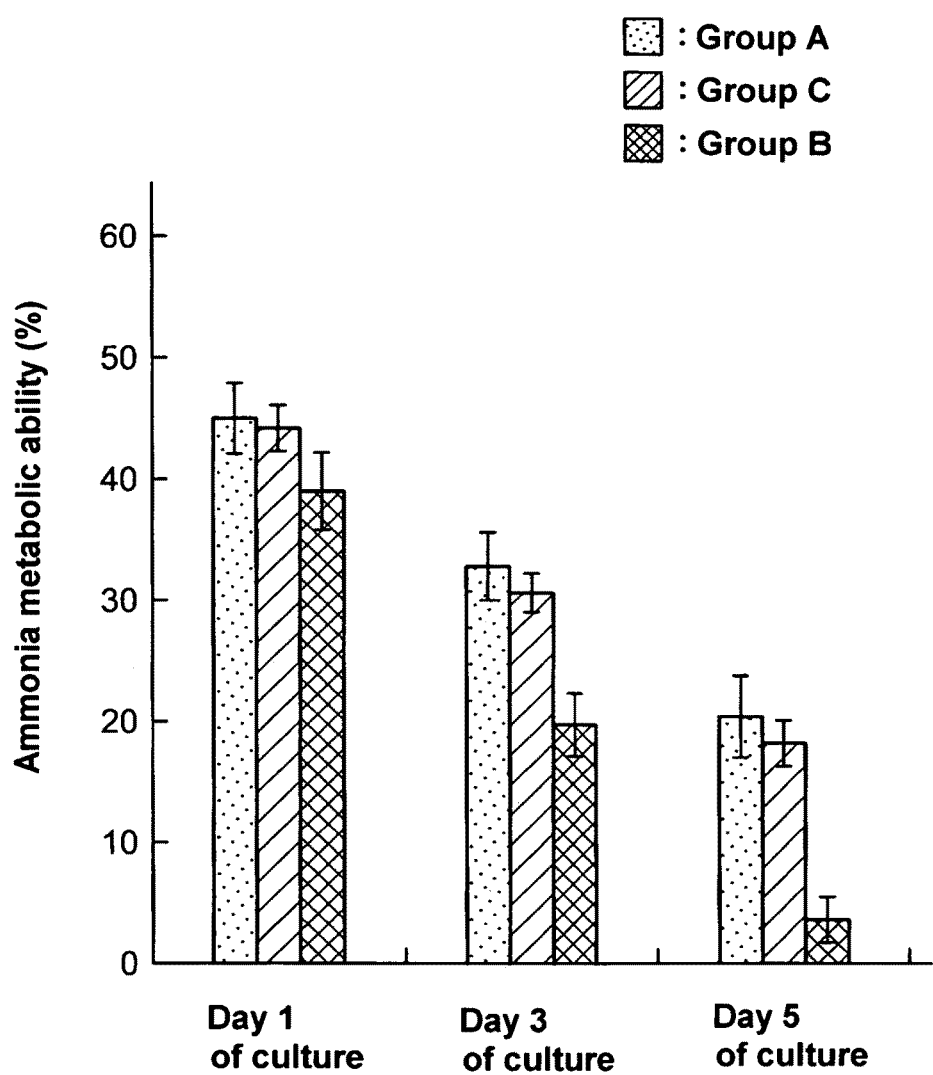
FIG. 8(b) is a graph comparing metabolic abilities of ammonia in human hepatocyte cultured by a cultivation method of the present invention using a peptide hydrogel as a scaffold (group A), human hepatocyte cultured by a conventional cultivation method using collagen as a scaffold (group B) and human hepatocyte cultured by a cultivation method using Matrigel as a scaffold (group C).

The metabolic abilities of ammonia in cultured human hepatocyte were measured and compared between groups A, B and C. Ammonium sulfate (0.56 mM) was added to human hepatocyte media on days 1, 3 and 5 of culture without insert, and the concentration of ammonia in the media after 24 hours was measured (FUJI DRI-CHEM SLIDE), and the metabolic rate was calculated. The results are shown in FIG. 8(b) and Table 4(b). In the group using PuraMatrix of SEQ ID NO:1 (group A), the ammonia metabolic rate was significantly better as compared with collagen type I (monolayer) (group B) and Matrigel (group C). The expression "culture medium only" in the graph and table means that culture medium only, containing no cells, is measured, and the significant difference was tested, using ANNOVA.

TABLE 4(b)

|  | Group A | Group C | Group B | Culture medium only |
|---|---|---|---|---|
| Day 1 of culture | 45.0 | 44.2 | 39.0 | 0.0 |
| Day 3 of culture | 32.8 | 30.6 | 19.7 | 0.0 |
| Day 5 of culture | 20.4 | 18.2 | 3.6 | 0.0 |
|  | Standard deviation | Standard deviation | Standard deviation | Standard deviation |
| Day 1 of culture | 2.9 | 1.9 | 3.2 | 0.0 |
| Day 3 of culture | 2.8 | 1.6 | 2.6 | 0.0 |
| Day 5 of culture | 3.4 | 1.9 | 1.9 | 0.0 |

Example 10

Culture of Porcine Pancreatic Islet

Large white male pigs (body weight: 15 to 20 kg) were used similarly to Example 1. 1.5 ml of ketalar for intramuscular injection was injected to induce sedation and then, auricular vein was acquired and 5 mg/kg of isozol and 1 mg/1 g of musculax were administered intravenously to achieve muscle relaxation. After endotracheal intubation, peritoneotomy was performed under general anesthesia with sevoflurene under controlled ventilation by an artificial respirator. A process of isolation of porcine pancreatic islet was carried out according to the method for isolation of human pancreatic islet (see, Lakey J R T, Kobayashi N, Shapiro A M J, Ricordi C, Okitsu T: Current human islet isolation protocol. Medical Review Co., Ltd., Osaka, Japan, 2004), and followed a method in a published literature (Yonekawa Y, Matsumono S, Okitsu T, Arata T, Iwanaga Y, Noguchi H, Nagata H, O'Neil J J, Tanaka K: Effective islet isolation method with extremely high islet yields from adult pigs. Cell Transplant. 14(10): 757-62, 2005). Those skilled in the art are capable of isolating pancreatic islet by referring to this literature. The isolated porcine pancreatic islets were suspended in William's Medium E supplemented with 10% fetal bovine serum, insulin $10^{-7}$ mol/l (available from SIGMA), dexametazone $10^{-6}$ mol/l (available from SIGMA), EGF 25 µg/ml, nicotineamide 10 mM (available from SIGMA), and antibiotic penicillin G/streptomycin (available from SIGMA), and 10 pancreatic islets were seeded on 6-well plates (without insert) coated with PuraMatrix of SEQ ID NO:1 (group A) and collagen type I (monolayer) (group B), respectively and then, cultured for 18 hours at 37° C. under 25 5% CO2.

Example 11

Morphological Study of Cultured Porcine Pancreatic Islet by Electron Microscope

Culture conditions of cultured porcine pancreatic islets were observed on day 5 of culture with an electron microscope and compared between groups A and B (see, FIG. 9). Scale bars in FIG. 9 show 100 pm in both the groups A and B. In the group using PuraMatrix of SEQ ID NO:1 (group A), cells kept spherical morphology, and in terms of morphology: 1. shape "spherical: 5 points", 2. border shape "well-rounded: 5 points", 3. integrity "solid/compact: 5 points" and 4. diameter "125 to 175 pm for whole cultured pancreatic islets: 3 points", sum thereof being 18 points (see, group A in FIG. 9). In contrast, porcine pancreatic islets cultured with collagen type I (monolayer) (group B) had irregular shape, and in terms of morphology: 1. shape "irregularly spherical: 3 points", 2. Border shape "approximately irregular: 2 points", 3. integrity "approximately fragmented: 2 points" and 4. diameter "less than 100 pm for whole cultured pancreatic islets: 1 point", sum thereof being 8 points (see, group B in FIG. 9).

Example 12

Measurement of Insulin Production Ability

Insulin production abilities of cultured porcine pancreatic islet were determined and compared between groups A and B. Using low glucose DMEM (glucose concentration: 100 g/l) (available from 25 GIBCO, Oakland, N.J.) supplemented with 10% FCS, nicotineamide 10 mM and penicillin G/streptomycin, cells were cultured for 24 hours until 60% confluency (low glucose). Then, the medium was changed for high glucose DMEM (glucose concentration: 450 g/l) (available from GIBCO, Oakland, N.J.) supplemented with 10% FCS, nicotineamide 10 mM and penicillin G/streptomycin, and cells were cultured for 6 hours (high glucose). After high glucose culture, the medium was exchanged for low glucose DMEM and cells were cultured for 6 hours (low glucose (after)). After each culture operation, the production amount of insulin in the culture medium (µg/l) was determined by an immunostaining method using a rabbit anti-human insulin antibody (available from DakoCytomation K. K., Kyoto, Japan). The results of staining are shown in FIG. 10 and Table 5. On day 5 of culture, in the group using PuraMatrix of SEQ ID NO:1 (group A), the amount of insulin secreted increased in high glucose concentration, and the amount of insulin secreted decreased in low glucose concentration. From these results, it was clarified that pancreatic islet obtained by the present invention retain a function of secreting insulin by response to the glucose concentration for a longer period of time, as compared with pancreatic islet cultured using collagen type I (monolayer) (group B) according to a conventional method. The expression "culture medium only" in the graph and table means that culture medium only, containing no cells, is measured, and the significant difference was tested, using ANNOVA.

TABLE 5

|  |  | Group A | Group B |
|---|---|---|---|
| Day 0 of culture | Low glucose | 0.80 | 0.80 |
|  | High glucose | 1.62 | 1.61 |
|  | Low glucose (after) | 1.01 | 0.99 |
|  | Culture medium only | 0.00 | 0.00 |
| Day 3 of culture | Low glucose | 0.80 | 0.50 |
|  | High glucose | 1.48 | 0.76 |
|  | Low glucose (after) | 0.90 | 0.65 |
|  | Culture medium only | 0.00 | 0.00 |
| Day 5 of culture | Low glucose | 0.69 | 0.37 |
|  | High glucose | 1.24 | 0.40 |
|  | Low glucose (after) | 0.78 | 0.40 |
|  | Culture medium only | 0.00 | 0.00 |
| Day 7 of culture | Low glucose | 0.49 | 0.10 |
|  | High glucose | 0.90 | 0.10 |
|  | Low glucose (after) | 0.71 | 0.10 |
|  | Culture medium only | 0.00 | 0.00 | unit: (µg/l)

Example 13

Culture of Human Pancreatic Islet

Healthy isolated human pancreatic islets provided from Alberta University in Canada (those skilled in the art can obtain them from Canada, Alberta University, human pancreatic islet transplantation program, Dr. Jonathan R T. Lakey) were seeded in a T25 10 culture flask. Human pancreatic islets were suspended in low glucose DMEM supplemented with 10% fetal bovine serum, insulin $10^{-7}$ mol/l, dexametazone $10^{-6}$ mol/l, EGF 25 µg/ml, nicotineamide 10 mM and antibiotic penicillin G/streptomycin, and 10 pancreatic islets were seeded on 6-well plates (without insert) coated with PuraMatrix of SEQ ID NO:1 (group A) or collagen type I (monolayer) (group B) and then, cultured for 18 hours at 37° C. under 5% CO2.

Example 14

Morphological Study of Cultured Human Pancreatic Islet by Electron 10 Microscope Culture conditions of cultured human pancreatic islets were observed on day 5 of culture with an electron microscope and compared between groups A and B (see, FIG. 11). Scale bars in FIG. 11 show 50 pm (group A) and 100 pm (group B), respectively. In the group using PuraMatrix of SEQ ID NO:1 (group A), cells kept spherical morphology, and in terms of morphology: 1. shape "spherical: 5 points", 2. border shape "irregularly spherical: 3 points", 3. integrity "solid/compact: 5 points" and 4. diameter "125 to 175 pm for whole cultured pancreatic islets: 3 points", sum thereof being 16 points (see, group A in FIG. 11). In contrast, porcine pancreatic islets cultured with collagen type I (monolayer) (group B) had irregular shape, and in terms of morphology: 1. shape "approximately flat: 2 points", 2. border shape "irregular: 1 point", 3. integrity "somewhat solid/compact: 3 points" and 4. diameter "125 to 175 pm for whole cultured pancreatic islets: 3 point", sum thereof being 9 points (see, group B in FIG. 11).

Example 15

Measurement of Insulin Production Ability

Insulin production abilities of cultured human pancreatic islet were determined and compared between groups A and B. Using low glucose DMEM (glucose concentration: 100 g/l) (available from GIBCO, Oakland, N.J.) supplemented with 10% FCS, nicotineamide 10 mM and penicillin G/streptomycin, cells were cultured for 24 hours until 60% confluency (low glucose). Then, the medium was changed for high glucose DMEM (glucose concentration: 450 g/l) (available from GIBCO, Oakland, N.J.) supplemented with 10% FCS, nicotineamide 10 mM and penicillin G/streptomycin, and cells were cultured for 6 hours (high glucose). After high glucose culture, the medium was exchanged for low glucose DMEM and cells were cultured for 6 hours (low glucose (after)). After respective culture operations, the production amount of insulin in the culture medium (µg/l) was determined by an immunostaining method using a rabbit anti-human insulin antibody (available from DakoCytomation K. K., Kyoto, Japan). The results of staining are shown in FIG. 12 and Table 6. On day 7 of culture, in the group using PuraMatrix of SEQ ID NO:1 (group A), the amount of insulin secreted increased in high glucose concentration, and the amount of insulin secreted decreased in low glucose concentration. From these results, it was clarified that pancreatic islet obtained by the present invention retain a function of secreting insulin by response to the glucose concentration for a longer period of time, as compared with pancreatic islet cultured using c ollagen type I (monolayer) (group B) according to a conventional method. The expression "culture medium only" in the graph and table means that culture medium only, containing no cells, is measured, and the significant difference was tested, using ANNOVA.

TABLE 6

|  |  | Group A | Group B |
|---|---|---|---|
| Day 1 of culture | Low glucose | 0.60 | 0.57 |
|  | High glucose | 1.89 | 1.73 |
|  | Low glucose (after) | 1.13 | 1.29 |
|  | Culture medium only | 0.00 | 0.00 |
| Day 3 of culture | Low glucose | 0.58 | 0.78 |
|  | High glucose | 1.68 | 1.32 |
|  | Low glucose (after) | 1.11 | 1.19 |
|  | Culture medium only | 0.00 | 0.00 |
| Day 5 of culture | Low glucose | 0.51 | 0.57 |
|  | High glucose | 1.43 | 0.66 |
|  | Low glucose (after) | 1.10 | 0.79 |
|  | Culture medium only | 0.00 | 0.00 |

TABLE 6-continued

|  |  | Group A | Group B |
|---|---|---|---|
| Day 7 of culture | Low glucose | 0.41 | 0.18 |
|  | High glucose | 0.76 | 0.12 |
|  | Low glucose (after) | 0.54 | 0.10 |
|  | Culture medium only | 0.00 | 0.00 | unit: (μg/l)

INDUSTRIAL APPLICABILITY

According to the present invention, by culturing a cell such as porcine hepatocyte, human hepatocyte, porcine pancreatic islet or human pancreatic islet using a peptide hydrogel as a scaffold, high-dimensional culture can be carried out for a long period under conditions where cell survival, cell morphology and cell functions are maintained.

The invention claimed is:

1. A method for culturing a primary cell in a cell culture, comprising:

providing differentiated functional primary cells selected from the group consisting of porcine pancreatic islets and human pancreatic islets;

culturing the differentiated functional primary cells using an insert and a self-assembling peptide hydrogel of SEQ ID NO:1;

evaluating the differentiated functional primary cells in the cell culture based on pancreatic islet morphology criteria;

assigning evaluation values of 1 to 5 points for each of the criteria consisting of:

shape having evaluation values of 1 point for flat shape, 2 points for approximately flat shape, 3 points for irregularly spherical shape, 4 points for approximately spherical shape, and 5 points for spherical shape;

border integrity having evaluation values of 1 point for irregular border, 2 points for approximately irregular border, 3 points for somewhat well-rounded border, 4 points for approximately well-rounded border and 5 points for well-rounded border;

cell integrity having evaluation values of 1 point for fragmented integrity, 2 points for approximately fragmented integrity, 3 points for somewhat solid/compact integrity, 4 points for approximately solid/compact integrity, and 5 points for solid/compact integrity; and cell diameter having evaluation values of 1 point for smaller than 100 μm diameter (all <100 μm), 2 points for 100 to 150 μm diameter, 3 points for 125 to 175 μM diameter, 4 points for 150 to 200 μm diameter, and 5 points for larger than 200 μm for at least 10% of individual cultured pancreatic islets (>10%>200 μm); and totaling the evaluation value points resulting in a sum evaluation value of 4 to 25 points.

2. The method of claim 1, wherein the sum evaluation value is at least 12 points.

3. The method of claim 1, wherein the porcine pancreatic islets or the human pancreatic islet cells produce insulin;
measuring the insulin; and
wherein the amount of insulin is 0.4 to 1.2 µg/l.

* * * * *